US011975092B2

(12) United States Patent
Mitchell et al.

(10) Patent No.: US 11,975,092 B2
(45) Date of Patent: *May 7, 2024

(54) HAIR TREATMENT COMPOSITIONS, METHODS, AND KITS FOR TREATING HAIR

(71) Applicant: L'Oreal, Paris (FR)

(72) Inventors: Barbara Mitchell, Teaneck, NJ (US); Anand Ramchandra Mahadeshwar, Powai (IN); Jacob Gordon, Clark, NJ (US)

(73) Assignee: L'OREAL, Paris (FR)

( * ) Notice: Subject to any disclaimer, the term of this patent is extended or adjusted under 35 U.S.C. 154(b) by 97 days.

This patent is subject to a terminal disclaimer.

(21) Appl. No.: 17/403,327

(22) Filed: Aug. 16, 2021

(65) Prior Publication Data

US 2021/0369591 A1 Dec. 2, 2021

Related U.S. Application Data

(63) Continuation of application No. 16/176,350, filed on Oct. 31, 2018, now Pat. No. 11,090,249.

(51) Int. Cl.
| | |
|---|---|
| *A61K 8/73* | (2006.01) |
| *A61G 5/06* | (2006.01) |
| *A61K 8/34* | (2006.01) |
| *A61K 8/362* | (2006.01) |
| *A61K 8/365* | (2006.01) |
| *A61K 8/41* | (2006.01) |
| *A61Q 5/00* | (2006.01) |
| *A61Q 5/06* | (2006.01) |

(52) U.S. Cl.
CPC .................. *A61K 8/73* (2013.01); *A61G 5/06* (2013.01); *A61K 8/345* (2013.01); *A61K 8/362* (2013.01); *A61K 8/365* (2013.01); *A61K 8/41* (2013.01); *A61Q 5/002* (2013.01)

(58) Field of Classification Search
CPC .......... A61K 8/73; A61K 8/343; A61K 8/362; A61K 8/365; A61K 8/41; A61Q 5/0002; A61Q 5/06
See application file for complete search history.

(56) References Cited

U.S. PATENT DOCUMENTS

| | | | |
|---|---|---|---|
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,674,580 A | 4/1954 | Henkin |
| 2,850,351 A | 9/1958 | Moore et al. |
| 2,961,347 A | 11/1960 | Floyd |
| 3,142,623 A | 7/1964 | Zviak et al. |
| 3,193,464 A | 7/1965 | Edman et al. |
| 3,206,462 A | 9/1965 | McCarty |
| 3,227,615 A | 1/1966 | Korden |
| 3,288,770 A | 11/1966 | Butler |
| 3,412,019 A | 11/1968 | Hoover et al. |
| 3,472,243 A | 10/1969 | Wall et al. |
| 3,472,840 A | 10/1969 | Stone et al. |
| 3,589,978 A | 6/1971 | Kamal et al. |
| 3,632,559 A | 1/1972 | Matter et al. |
| 3,766,267 A | 10/1973 | Zak et al. |
| 3,840,656 A | 10/1974 | Kalopissis et al. |
| 3,874,870 A | 4/1975 | Green et al. |
| 3,917,817 A | 11/1975 | Vanlerberghe et al. |
| 3,929,990 A | 12/1975 | Green et al. |
| 3,966,904 A | 6/1976 | Green et al. |
| 4,001,432 A | 1/1977 | Green et al. |
| 4,003,699 A | 1/1977 | Rose et al. |
| 4,005,193 A | 1/1977 | Green et al. |
| 4,012,398 A | 3/1977 | Conner et al. |
| 4,013,787 A | 3/1977 | Vanlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,020 A | 5/1977 | Green et al. |

(Continued)

FOREIGN PATENT DOCUMENTS

| | | |
|---|---|---|
| CN | 1383377 A | 12/2002 |
| CN | 1423548 A | 6/2003 |

(Continued)

OTHER PUBLICATIONS

Translation of Notice of Reasons for Rejection for Application No. 2022-020688, dated Jan. 10, 2023.
Non-Final Office Action for copending U.S. Appl. No. 17/356,131, dated Jan. 19, 2023 (now abandoned).
Translation of Decision on Rejection for counterpart CN Application No. 201880034056.5, dated Jan. 9, 2023.
Translation of Chinese Second Office Action for counterpart Application No. 201880084390.1, dated Feb. 18, 2023.

(Continued)

*Primary Examiner* — Shirley V Gembeh
(74) *Attorney, Agent, or Firm* — THE MARBURY LAW GROUP, PLLC

(57) ABSTRACT

The instant disclosure relates to hair treatment compositions that include a unique combination of components that function to impart desirable cosmetic properties to the hair. The hair treatment compositions typically include:

at least 0.5 wt. % of at least one non-polymeric mono, di, or tricarboxylic acid, and/or a salt thereof;

one or more amines selected from the group consisting of diamines, polyamines, alkylamines, alkanolamines, and a mixture thereof;

one or more fructan polysaccharides;

one or more prosolvents; and water.

19 Claims, No Drawings

(56) References Cited

U.S. PATENT DOCUMENTS

| | | |
|---|---|---|
| 4,031,307 A | 6/1977 | DeMartino et al. |
| 4,075,136 A | 2/1978 | Schaper |
| 4,131,576 A | 12/1978 | Tovine et al. |
| 4,166,894 A | 9/1979 | Schaper |
| 4,172,887 A | 10/1979 | Vanlerberghe et al. |
| RE30,199 E | 1/1980 | Rose et al. |
| 4,189,468 A | 2/1980 | Vanlerberghe et al. |
| 4,197,865 A | 4/1980 | Jacquet et al. |
| 4,217,914 A | 8/1980 | Jacquet et al. |
| 4,240,450 A | 12/1980 | Grollier et al. |
| 4,277,581 A | 7/1981 | Vanlerberghe et al. |
| 4,348,202 A | 9/1982 | Grollier et al. |
| 4,349,532 A | 9/1982 | Vanlerberghe et al. |
| 4,381,919 A | 5/1983 | Jacquet et al. |
| 4,412,943 A | 11/1983 | Hirota et al. |
| 4,422,853 A | 12/1983 | Jacquet et al. |
| 4,425,132 A | 1/1984 | Grollier et al. |
| 4,532,950 A | 8/1985 | Lang et al. |
| 4,579,732 A | 4/1986 | Grollier et al. |
| 4,591,610 A | 5/1986 | Grollier |
| 4,608,250 A | 8/1986 | Jacquet et al. |
| 4,734,277 A | 3/1988 | Login |
| 4,761,273 A | 8/1988 | Grollier et al. |
| 4,770,873 A | 9/1988 | Wolfram et al. |
| 4,772,462 A | 9/1988 | Boothe et al. |
| 4,777,040 A | 10/1988 | Grollier et al. |
| 4,793,992 A | 12/1988 | Mathews et al. |
| 4,793,993 A | 12/1988 | Siuta-Mangano et al. |
| 4,812,307 A | 3/1989 | Siuta-Mangano |
| 4,834,971 A | 5/1989 | Klenk et al. |
| 4,855,130 A | 8/1989 | Konrad et al. |
| 4,906,460 A | 3/1990 | Kim et al. |
| 4,948,579 A | 8/1990 | Jacquet et al. |
| 4,970,066 A | 11/1990 | Grollier et al. |
| 5,061,289 A | 10/1991 | Clausen et al. |
| 5,085,860 A | 2/1992 | Junino et al. |
| 5,091,171 A | 2/1992 | Yu et al. |
| 5,143,518 A | 9/1992 | Madrange et al. |
| 5,196,189 A | 3/1993 | Jacquet et al. |
| 5,221,286 A | 6/1993 | Singleton et al. |
| 5,293,885 A | 3/1994 | Darkwa et al. |
| 5,350,572 A | 9/1994 | Savaides et al. |
| 5,356,438 A | 10/1994 | Kim et al. |
| 5,380,340 A | 1/1995 | Neunhoeffer et al. |
| 5,534,267 A | 7/1996 | Neunhoeffer et al. |
| 5,565,216 A | 10/1996 | Cowsar et al. |
| 5,593,662 A | 1/1997 | Deckner et al. |
| 5,616,150 A | 4/1997 | Moeller et al. |
| 5,628,991 A | 5/1997 | Samain et al. |
| 5,635,168 A | 6/1997 | Burns et al. |
| 5,651,960 A | 7/1997 | Chan et al. |
| 5,656,265 A | 8/1997 | Bailey et al. |
| 5,663,366 A | 9/1997 | Neunhoeffer et al. |
| 5,688,291 A | 11/1997 | Said et al. |
| 5,708,151 A | 1/1998 | Möckli |
| 5,750,099 A | 5/1998 | Yoshihara et al. |
| 5,766,576 A | 6/1998 | Löwe et al. |
| 5,785,962 A | 7/1998 | Hinz et al. |
| 5,811,085 A | 9/1998 | Halloran |
| 5,833,966 A | 11/1998 | Samain |
| 5,853,706 A | 12/1998 | Klar |
| 5,853,706 A | 12/1998 | Klar |
| 5,853,707 A | 12/1998 | Wells et al. |
| 5,869,068 A | 2/1999 | De Lacharriere et al. |
| 5,951,969 A | 9/1999 | Golinski et al. |
| 5,972,322 A | 10/1999 | Rath et al. |
| 5,985,803 A | 11/1999 | Rizvi et al. |
| 6,013,250 A | 1/2000 | Cannell et al. |
| 6,015,574 A | 1/2000 | Cannell et al. |
| 6,036,966 A | 3/2000 | Youssefyeh |
| 6,090,762 A | 7/2000 | Clapperton et al. |
| 6,099,592 A | 8/2000 | Vidal et al. |
| 6,173,717 B1 | 1/2001 | Schonert et al. |
| 6,231,843 B1 | 5/2001 | Hoelzel et al. |
| 6,241,971 B1 | 6/2001 | Fox et al. |
| 6,284,003 B1 | 9/2001 | Rose et al. |
| 6,309,426 B1 | 10/2001 | Dias et al. |
| 6,338,741 B1 | 1/2002 | Vidal et al. |
| 6,348,189 B1 | 2/2002 | Tanabe et al. |
| 6,348,200 B1 | 2/2002 | Nakajima et al. |
| 6,358,502 B1 | 3/2002 | Tanabe et al. |
| 6,398,821 B1 | 6/2002 | Dias et al. |
| 6,458,906 B1 | 10/2002 | Torgerson et al. |
| 6,488,945 B2 | 12/2002 | Sato |
| 6,515,050 B1 | 2/2003 | Mitsuzuka et al. |
| 6,537,532 B1 | 3/2003 | Torgerson et al. |
| 6,562,327 B1 | 5/2003 | Nguyen et al. |
| 6,569,412 B2 | 5/2003 | Yamaguchi et al. |
| 6,645,258 B2 | 11/2003 | Vidal et al. |
| 6,645,478 B2 | 11/2003 | Rollat et al. |
| 6,669,933 B2 | 12/2003 | Duffer et al. |
| 6,706,258 B1 | 3/2004 | Gallagher et al. |
| 6,730,789 B1 | 5/2004 | Birault et al. |
| 6,767,875 B1 | 7/2004 | Snyder et al. |
| 6,979,439 B1 | 12/2005 | Sakai et al. |
| 6,984,250 B1 | 1/2006 | Legrand et al. |
| 7,041,142 B2 | 5/2006 | Chan et al. |
| 7,044,986 B2 | 5/2006 | Ogawa et al. |
| 7,135,167 B2 | 11/2006 | Legrand et al. |
| 7,147,843 B2 | 12/2006 | Yoshida et al. |
| 7,151,079 B2 | 12/2006 | Fack et al. |
| 7,204,861 B2 | 4/2007 | Marsh et al. |
| 7,390,479 B2 | 6/2008 | Sockel et al. |
| 7,427,656 B2 | 9/2008 | Decarolis et al. |
| 7,495,037 B2 | 2/2009 | Moszner et al. |
| 7,598,213 B2 | 10/2009 | Geary et al. |
| 7,612,141 B2 | 11/2009 | Sakai et al. |
| 7,815,901 B2 | 10/2010 | Mathonneau et al. |
| 7,905,926 B2 | 3/2011 | DeGeorge et al. |
| 7,915,208 B2 | 3/2011 | Roso et al. |
| 7,931,698 B2 | 4/2011 | Simonet et al. |
| 7,972,388 B2 | 7/2011 | Hamilton et al. |
| 7,981,405 B2 | 7/2011 | Ueyama et al. |
| 8,163,861 B2 | 4/2012 | Puerta et al. |
| 8,241,370 B2 | 8/2012 | Legrand et al. |
| 8,288,329 B2 | 10/2012 | Hata et al. |
| 8,298,519 B2 | 10/2012 | Adams et al. |
| 8,357,356 B2 | 1/2013 | Zaeska et al. |
| 8,388,701 B2 | 3/2013 | Uellner et al. |
| 8,513,200 B2 | 8/2013 | Dixon et al. |
| 8,613,913 B2 | 12/2013 | Chang et al. |
| 8,632,758 B2 | 1/2014 | Terada |
| 8,642,021 B2 | 2/2014 | Brautigam et al. |
| 8,921,292 B2 | 12/2014 | Fujita et al. |
| 9,006,162 B1 | 4/2015 | Rizk |
| 9,044,409 B2 | 6/2015 | Carola et al. |
| 9,095,518 B2 | 8/2015 | Pressly et al. |
| 9,114,088 B2 | 8/2015 | Konno et al. |
| 9,144,537 B1 | 9/2015 | Pressly et al. |
| 9,175,114 B2 | 11/2015 | Puerta et al. |
| 9,180,086 B2 | 11/2015 | Cabourg et al. |
| 9,283,156 B2 | 3/2016 | Savaides et al. |
| 9,326,926 B2 | 5/2016 | Pressly et al. |
| 9,402,796 B2 | 8/2016 | Briggs et al. |
| 9,498,419 B2 | 11/2016 | Pressly et al. |
| 9,597,273 B2 | 3/2017 | Pressly et al. |
| 9,610,241 B2 | 4/2017 | Cabourg et al. |
| 9,849,071 B2 | 12/2017 | Fack et al. |
| 9,918,923 B1 | 3/2018 | Naiberk et al. |
| 9,993,406 B2 | 6/2018 | Manneck et al. |
| 10,004,673 B1 | 6/2018 | Elsen-Wahrer et al. |
| 10,085,931 B2 | 10/2018 | Baghdadli et al. |
| 10,219,994 B2 | 3/2019 | Lechner et al. |
| 10,231,915 B2 | 3/2019 | Dreher et al. |
| 10,561,599 B2 | 2/2020 | Patterson et al. |
| 10,576,307 B2 | 3/2020 | Patterson et al. |
| 11,596,588 B2 | 3/2023 | Machover et al. |
| 2001/0029637 A1 | 10/2001 | Nakashimada et al. |
| 2001/0042276 A1 | 11/2001 | Kawasoe et al. |
| 2001/0052354 A1 | 12/2001 | Nishibe et al. |
| 2002/0029429 A1 | 3/2002 | Dias et al. |
| 2002/0032933 A1 | 3/2002 | Dias et al. |
| 2002/0050013 A1 | 5/2002 | Vidal et al. |
| 2002/0053110 A1 | 5/2002 | Dias et al. |

(56) References Cited

U.S. PATENT DOCUMENTS

| | | |
|---|---|---|
| 2002/0155081 A1 | 10/2002 | Coope |
| 2002/0189034 A1 | 12/2002 | Kitabata et al. |
| 2003/0012761 A1 | 1/2003 | Yoshida et al. |
| 2003/0019051 A9 | 1/2003 | Vidal et al. |
| 2003/0049222 A1 | 3/2003 | Akhter et al. |
| 2003/0072962 A1 | 4/2003 | Matsuzaki et al. |
| 2003/0074743 A1 | 4/2003 | Noguchi et al. |
| 2003/0083380 A1 | 5/2003 | Yu et al. |
| 2003/0152543 A1 | 8/2003 | Legrand et al. |
| 2003/0215415 A1 | 11/2003 | Mitsumatsu et al. |
| 2004/0034944 A1 | 2/2004 | Legrand et al. |
| 2004/0034946 A1 | 2/2004 | Legrand et al. |
| 2004/0067212 A1 | 4/2004 | Tokuyama et al. |
| 2004/0086475 A1 | 5/2004 | Boswell et al. |
| 2004/0088800 A1 | 5/2004 | Cotteret |
| 2004/0156877 A1 | 8/2004 | Tokuyama et al. |
| 2004/0181883 A1 | 9/2004 | Legrand et al. |
| 2004/0202689 A1 | 10/2004 | Subramanyan et al. |
| 2004/0216244 A1 | 11/2004 | Cotteret et al. |
| 2004/0228580 A1 | 11/2004 | Lee et al. |
| 2004/0241114 A1 | 12/2004 | Gupta |
| 2004/0256598 A1 | 12/2004 | Plos et al. |
| 2004/0258652 A1 | 12/2004 | Pascaly et al. |
| 2005/0015894 A1 | 1/2005 | Cottard et al. |
| 2005/0036970 A1 | 2/2005 | Sabbagh et al. |
| 2005/0087718 A1 | 4/2005 | Okada |
| 2005/0095215 A1 | 5/2005 | Popp |
| 2005/0176615 A1 | 8/2005 | Kinoshita et al. |
| 2005/0186164 A1 | 8/2005 | Akyuz |
| 2005/0191263 A1 | 9/2005 | Ueyama et al. |
| 2005/0193501 A1 | 9/2005 | Chan et al. |
| 2005/0201966 A1 | 9/2005 | Ueyama et al. |
| 2006/0024257 A1 | 2/2006 | Chang et al. |
| 2006/0045862 A1 | 3/2006 | Tada et al. |
| 2006/0062751 A1 | 3/2006 | Sato et al. |
| 2006/0075580 A1 | 4/2006 | Chan et al. |
| 2006/0093571 A1 | 5/2006 | Glinski |
| 2006/0135397 A1 | 6/2006 | Bissey-Beugras et al. |
| 2006/0166845 A1 | 7/2006 | Terada |
| 2006/0182702 A1 | 8/2006 | Lazzeri et al. |
| 2006/0198807 A1 | 9/2006 | Morioka |
| 2006/0228316 A1 | 10/2006 | Cannell et al. |
| 2006/0251673 A1 | 11/2006 | Hwang et al. |
| 2006/0276369 A1 | 12/2006 | Levecke et al. |
| 2007/0041921 A1 | 2/2007 | Neill et al. |
| 2007/0067924 A1 | 3/2007 | Beck et al. |
| 2007/0107142 A1 | 5/2007 | Nguyen et al. |
| 2007/0116661 A1 | 5/2007 | Mata |
| 2007/0160560 A1 | 7/2007 | Laurent et al. |
| 2007/0161543 A1 | 7/2007 | Yu et al. |
| 2007/0190008 A1 | 8/2007 | Campain et al. |
| 2007/0261594 A1 | 11/2007 | Vaskelis et al. |
| 2007/0264208 A1 | 11/2007 | Mougin et al. |
| 2008/0025937 A1 | 1/2008 | Cassier |
| 2008/0025939 A1 | 1/2008 | Cassier et al. |
| 2008/0066773 A1 | 3/2008 | Anderson et al. |
| 2008/0118458 A1 | 5/2008 | Giesen et al. |
| 2008/0124295 A1 | 5/2008 | Duranton et al. |
| 2008/0138309 A1 | 6/2008 | Malle et al. |
| 2008/0141468 A1 | 6/2008 | Cotteret |
| 2008/0187506 A1 | 8/2008 | Carballada et al. |
| 2008/0226576 A1 | 9/2008 | Benabdillah et al. |
| 2008/0233072 A1 | 9/2008 | Bureiko et al. |
| 2008/0306025 A1 | 12/2008 | Yu et al. |
| 2009/0022681 A1 | 1/2009 | Carballada et al. |
| 2009/0041699 A1 | 2/2009 | Molenda et al. |
| 2009/0041701 A1 | 2/2009 | Taylor |
| 2009/0041713 A1 | 2/2009 | Taylor |
| 2009/0053165 A1 | 2/2009 | Brown et al. |
| 2009/0071493 A1 | 3/2009 | Nguyen et al. |
| 2009/0074683 A1 | 3/2009 | Nguyen et al. |
| 2009/0126756 A1 | 5/2009 | Syed et al. |
| 2009/0208499 A1 | 8/2009 | Yu et al. |
| 2009/0214628 A1 | 8/2009 | de Rijk |
| 2009/0252697 A1 | 10/2009 | Barbarat et al. |
| 2009/0274677 A1 | 11/2009 | Isaacs et al. |
| 2010/0004391 A1 | 1/2010 | Haddleton et al. |
| 2010/0015079 A1 | 1/2010 | Schrader |
| 2010/0081716 A1 | 4/2010 | Matsunaga et al. |
| 2010/0119468 A1 | 5/2010 | Garcia Castro et al. |
| 2010/0154140 A1 | 6/2010 | Simonet et al. |
| 2010/0158845 A1 | 6/2010 | Ellington et al. |
| 2010/0158964 A1 | 6/2010 | Cunningham et al. |
| 2010/0178267 A1 | 7/2010 | Puerta et al. |
| 2010/0189795 A1 | 7/2010 | Dreher |
| 2010/0202998 A1 | 8/2010 | Ramos-Stanbury et al. |
| 2010/0247463 A1 | 9/2010 | Yu et al. |
| 2010/0303748 A1 | 12/2010 | Hercouet |
| 2011/0056508 A1 | 3/2011 | Gross et al. |
| 2011/0061671 A1 | 3/2011 | Neplaz et al. |
| 2011/0142778 A1 | 6/2011 | Hloucha et al. |
| 2011/0150804 A1* | 6/2011 | Nojiri .................... A61K 8/365 424/70.1 |
| 2011/0213033 A1 | 9/2011 | Tokuyama et al. |
| 2011/0256084 A1 | 10/2011 | Dixon et al. |
| 2011/0311463 A1 | 12/2011 | Diamond et al. |
| 2012/0015894 A1 | 1/2012 | Terada |
| 2012/0022037 A1 | 1/2012 | Terada |
| 2012/0064137 A1 | 3/2012 | Kawai |
| 2012/0114583 A1 | 5/2012 | Giesen et al. |
| 2012/0118316 A1 | 5/2012 | Uellner et al. |
| 2012/0121705 A1 | 5/2012 | Paus et al. |
| 2012/0142569 A1 | 6/2012 | Cao et al. |
| 2012/0142569 A1 | 6/2012 | Cao et al. |
| 2012/0180807 A1 | 7/2012 | Flohr |
| 2012/0230935 A1 | 9/2012 | Kim et al. |
| 2012/0244082 A1 | 9/2012 | Sulzbach et al. |
| 2012/0288459 A1 | 11/2012 | Burg et al. |
| 2012/0329650 A1 | 12/2012 | Lopez-Cervantes |
| 2013/0016246 A1 | 1/2013 | Hatanaka et al. |
| 2013/0034515 A1 | 2/2013 | Stone et al. |
| 2013/0102513 A1 | 4/2013 | Terada |
| 2013/0118996 A1 | 5/2013 | Kaplan |
| 2013/0142748 A1 | 6/2013 | Tamura et al. |
| 2013/0142748 A1 | 6/2013 | Tamura et al. |
| 2013/0149274 A1 | 6/2013 | Nguyen et al. |
| 2013/0152959 A1 | 6/2013 | Genain et al. |
| 2013/0156716 A1 | 6/2013 | Yontz |
| 2013/0164240 A1 | 6/2013 | Schrott |
| 2013/0172518 A1 | 7/2013 | Huang et al. |
| 2013/0216491 A1 | 8/2013 | Ogihara et al. |
| 2013/0233331 A1 | 9/2013 | Khenniche et al. |
| 2013/0233332 A1 | 9/2013 | Khenniche et al. |
| 2013/0251656 A1 | 9/2013 | Khenniche et al. |
| 2013/0266529 A1 | 10/2013 | Deconinck et al. |
| 2013/0280199 A1 | 10/2013 | Albert et al. |
| 2013/0309190 A1 | 11/2013 | Dimotakis et al. |
| 2013/0315852 A1 | 11/2013 | Streuli |
| 2014/0120047 A1 | 5/2014 | Krueger |
| 2014/0158150 A1 | 6/2014 | Schoepgens et al. |
| 2014/0170105 A1 | 6/2014 | Chen et al. |
| 2014/0171354 A1 | 6/2014 | Miralles et al. |
| 2014/0186283 A1 | 7/2014 | Cabourg et al. |
| 2014/0196741 A1 | 7/2014 | Cabourg et al. |
| 2014/0246041 A1 | 9/2014 | Krueger |
| 2014/0256885 A1 | 9/2014 | Puerta et al. |
| 2015/0004117 A1 | 1/2015 | Tan et al. |
| 2015/0004119 A1 | 1/2015 | Tan et al. |
| 2015/0034117 A1 | 2/2015 | Pressly et al. |
| 2015/0034119 A1 | 2/2015 | Pressly et al. |
| 2015/0037270 A1 | 2/2015 | Pressly et al. |
| 2015/0037271 A1 | 2/2015 | Pressly et al. |
| 2015/0053228 A1 | 2/2015 | Bonauer et al. |
| 2015/0053230 A1 | 2/2015 | Myatt |
| 2015/0090285 A1 | 4/2015 | Worner et al. |
| 2015/0157544 A1 | 6/2015 | Briggs et al. |
| 2015/0252302 A1 | 9/2015 | Rieth et al. |
| 2015/0283041 A1 | 10/2015 | Benn et al. |
| 2015/0290101 A1 | 10/2015 | Pressly et al. |
| 2015/0297496 A1 | 10/2015 | Kroon et al. |
| 2015/0305469 A1 | 10/2015 | Paul |
| 2015/0313816 A1 | 11/2015 | Daubresse |
| 2015/0328102 A1 | 11/2015 | Pressly et al. |
| 2016/0058688 A1 | 3/2016 | Anderheggen et al. |

(56) References Cited

U.S. PATENT DOCUMENTS

| | | | |
|---|---|---|---|
| 2016/0081899 A1 | 3/2016 | Pressly et al. |
| 2016/0166479 A1 | 6/2016 | Chiou et al. |
| 2016/0175238 A1 | 6/2016 | Shin et al. |
| 2016/0193129 A1 | 7/2016 | Pressly et al. |
| 2016/0235649 A1 | 8/2016 | Streuli |
| 2016/0263003 A1 | 9/2016 | Pressly et al. |
| 2016/0310394 A1 | 10/2016 | Pressly et al. |
| 2016/0331664 A1 | 11/2016 | Anderheggen et al. |
| 2016/0348037 A1 | 12/2016 | Findlay et al. |
| 2017/0007518 A1 | 1/2017 | Everaert et al. |
| 2017/0112740 A1 | 4/2017 | Schoepgens et al. |
| 2017/0112743 A1 | 4/2017 | Schoepgens et al. |
| 2017/0113071 A1 | 4/2017 | Schoepgens et al. |
| 2017/0119122 A1 | 5/2017 | Rautenberg-Groth et al. |
| 2017/0128334 A1 | 5/2017 | Schoepgens et al. |
| 2017/0128342 A1 | 5/2017 | Schoepgens et al. |
| 2017/0143611 A1 | 5/2017 | Hippe et al. |
| 2017/0151143 A1 | 6/2017 | Scheunemann et al. |
| 2017/0151144 A1 | 6/2017 | Scheunemann et al. |
| 2017/0151146 A1 | 6/2017 | Scheunemann et al. |
| 2017/0151147 A1 | 6/2017 | Scheunemann et al. |
| 2017/0151156 A1 | 6/2017 | Scheunemann et al. |
| 2017/0157011 A1 | 6/2017 | Punyani et al. |
| 2017/0165161 A1 | 6/2017 | Manneck et al. |
| 2017/0202763 A1 | 7/2017 | Manneck et al. |
| 2017/0246094 A1 | 8/2017 | Dreher et al. |
| 2017/0252291 A1 | 9/2017 | Lechner et al. |
| 2017/0360658 A1 | 12/2017 | Ferrari et al. |
| 2018/0055751 A1 | 3/2018 | Gevgilili et al. |
| 2018/0116942 A1 | 5/2018 | Mahadeshwar et al. |
| 2018/0140531 A1 | 5/2018 | Singer et al. |
| 2018/0140532 A1 | 5/2018 | Singer et al. |
| 2018/0280267 A1 | 10/2018 | Rughani et al. |
| 2018/0280269 A1 | 10/2018 | Rughani et al. |
| 2018/0280270 A1 | 10/2018 | Rughani et al. |
| 2018/0280271 A1 | 10/2018 | Fack et al. |
| 2018/0338895 A1 | 11/2018 | Patterson et al. |
| 2018/0338901 A1 | 11/2018 | Patterson et al. |
| 2018/0339175 A1 | 11/2018 | Patterson et al. |
| 2019/0160000 A1 | 5/2019 | Herrlein et al. |
| 2019/0201309 A1 | 7/2019 | Machover et al. |
| 2020/0129405 A1 | 4/2020 | Mitchell et al. |

FOREIGN PATENT DOCUMENTS

| | | |
|---|---|---|
| CN | 1424016 A | 6/2003 |
| CN | 1454074 A | 11/2003 |
| CN | 1678281 A | 10/2005 |
| CN | 1717215 A | 1/2006 |
| CN | 1778289 A | 5/2006 |
| CN | 1798539 A | 7/2006 |
| CN | 101282705 A | 10/2008 |
| CN | 101495087 A | 7/2009 |
| CN | 101686920 A | 3/2010 |
| CN | 101843561 A | 9/2010 |
| CN | 101966136 A | 2/2011 |
| CN | 102056896 A | 5/2011 |
| CN | 102166163 A | 8/2011 |
| CN | 102231974 A | 11/2011 |
| CN | 102281864 A | 12/2011 |
| CN | 102361627 A | 2/2012 |
| CN | 102397232 A | 4/2012 |
| CN | 102451117 A | 5/2012 |
| CN | 103356395 A | 10/2013 |
| CN | 103998099 A | 8/2014 |
| CN | 104066419 A | 9/2014 |
| CN | 104066423 A | 9/2014 |
| CN | 104066423 A | 9/2014 |
| CN | 104159567 A | 11/2014 |
| CN | 104519962 A | 4/2015 |
| CN | 105267066 A | 1/2016 |
| CN | 105902403 A | 8/2016 |
| CN | 105902404 A | 8/2016 |
| CN | 106265109 A | 1/2017 |
| DE | 1220969 B | 7/1966 |
| DE | 2225541 A1 | 12/1973 |
| DE | 2359399 | 6/1976 |
| DE | 3843892 A1 | 6/1990 |
| DE | 4133957 A1 | 4/1993 |
| DE | 4300320 A2 | 7/1994 |
| DE | 19543988 A1 | 5/1997 |
| DE | 29722990 U1 | 5/1999 |
| DE | 10051773 A2 | 4/2002 |
| DE | 10051774 A2 | 4/2002 |
| DE | 20208254 U1 | 8/2002 |
| DE | 102004052480 A1 | 5/2006 |
| DE | 102007039745 A1 | 2/2009 |
| DE | 202015104742 U1 | 10/2015 |
| DE | 102014213317 A1 | 1/2016 |
| DE | 102015223828 A1 | 9/2016 |
| DE | 102015221460 A1 | 5/2017 |
| DE | 102016200688 A1 | 7/2017 |
| DE | 202017001430 U1 | 7/2017 |
| EP | 0122324 A1 | 10/1984 |
| EP | 0159628 A2 | 10/1985 |
| EP | 0286261 A2 | 10/1988 |
| EP | 0298684 A2 | 1/1989 |
| EP | 0299764 A2 | 1/1989 |
| EP | 0437114 A1 | 7/1991 |
| EP | 0512879 A2 | 11/1992 |
| EP | 0636358 A1 | 2/1995 |
| EP | 0714954 A2 | 6/1996 |
| EP | 0770375 A1 | 5/1997 |
| EP | 0855178 A2 | 7/1998 |
| EP | 0978272 A1 | 2/2000 |
| EP | 1118319 A1 | 7/2001 |
| EP | 1174112 A2 | 1/2002 |
| EP | 1216023 B1 | 4/2005 |
| EP | 1541117 A1 | 6/2005 |
| EP | 1570832 A1 | 9/2005 |
| EP | 1216022 B1 | 4/2006 |
| EP | 1690524 A2 | 8/2006 |
| EP | 1779896 A2 | 5/2007 |
| EP | 1810657 A1 | 7/2007 |
| EP | 2123250 A1 | 11/2009 |
| EP | 2165697 A1 | 3/2010 |
| EP | 2229933 A1 | 9/2010 |
| EP | 2295029 A1 | 3/2011 |
| EP | 2460511 A1 | 6/2012 |
| EP | 2471504 A1 | 7/2012 |
| EP | 2478892 A1 | 7/2012 |
| EP | 1510197 B1 | 3/2016 |
| FR | 1492597 A | 8/1967 |
| FR | 1583363 A | 10/1969 |
| FR | 2162025 A | 7/1973 |
| FR | 2252840 A1 | 6/1975 |
| FR | 2270846 A1 | 12/1975 |
| FR | 2280361 A2 | 2/1976 |
| FR | 2316271 A1 | 1/1977 |
| FR | 2320330 A1 | 3/1977 |
| FR | 2336434 A1 | 7/1977 |
| FR | 2368508 A2 | 5/1978 |
| FR | 2413907 A1 | 8/1979 |
| FR | 2505348 A1 | 11/1982 |
| FR | 2542997 A1 | 9/1984 |
| FR | 2733749 A1 | 11/1996 |
| FR | 2789895 A1 | 8/2000 |
| FR | 2789896 A1 | 8/2000 |
| FR | 2801308 A1 | 5/2001 |
| FR | 2841129 A1 | 12/2003 |
| FR | 2886136 A1 | 12/2006 |
| FR | 2939030 A1 | 6/2010 |
| FR | 2944441 A1 | 10/2010 |
| FR | 2966352 A1 | 4/2012 |
| FR | 2975899 A1 | 12/2012 |
| FR | 2975900 A1 | 12/2012 |
| GB | 713675 A | 8/1954 |
| GB | 741307 A | 11/1955 |
| GB | 773559 A | 4/1957 |
| GB | 1026978 A | 4/1966 |
| GB | 1125794 A | 8/1968 |
| GB | 1153196 A | 5/1969 |
| GB | 1260451 A | 1/1972 |
| GB | 1546809 A | 5/1979 |

(56) References Cited

FOREIGN PATENT DOCUMENTS

| | | |
|---|---|---|
| GB | 1584364 A | 2/1981 |
| GB | 2270259 A | 3/1994 |
| GB | 2270259 A | 3/1994 |
| JP | S60-158105 A | 8/1985 |
| JP | S62-212313 A | 9/1987 |
| JP | 63-154611 A | 6/1988 |
| JP | S63-239209 A | 10/1988 |
| JP | S63-255214 A | 10/1988 |
| JP | 02-019576 A | 1/1990 |
| JP | H02-138110 A | 5/1990 |
| JP | 05-163124 A | 6/1993 |
| JP | H07-069847 A | 3/1995 |
| JP | 08-198732 A | 8/1996 |
| JP | H08-509478 A | 10/1996 |
| JP | H09-249538 A | 9/1997 |
| JP | H10-203923 A | 8/1998 |
| JP | 2000-229821 A | 8/2000 |
| JP | 2001-081013 A | 3/2001 |
| JP | 2002-097115 A | 4/2002 |
| JP | 2002-105493 A | 4/2002 |
| JP | 2002-121121 A | 4/2002 |
| JP | 2002-356408 A | 12/2002 |
| JP | 2002-363048 A | 12/2002 |
| JP | 2003-095876 A | 4/2003 |
| JP | 2003-516335 A | 5/2003 |
| JP | 2004-026834 A | 1/2004 |
| JP | 2004-026976 A | 1/2004 |
| JP | 2005-060398 A | 3/2005 |
| JP | 2005-154348 A | 6/2005 |
| JP | 2006-052178 A | 2/2006 |
| JP | 2006-219493 A | 8/2006 |
| JP | 2006-316012 A | 11/2006 |
| JP | 2006-327994 A | 12/2006 |
| JP | 2008-169183 A | 7/2008 |
| JP | 2008-189686 A | 8/2008 |
| JP | 2009-007283 A | 1/2009 |
| JP | 2009-078992 A | 4/2009 |
| JP | 2009-536619 A | 10/2009 |
| JP | 2010-155823 A | 7/2010 |
| JP | 2011-042586 A | 3/2011 |
| JP | 2012-515218 A | 7/2012 |
| JP | 2013-500328 A | 1/2013 |
| JP | 2015-086211 A | 5/2015 |
| JP | 2016-003185 A | 1/2016 |
| JP | 2017-095451 A | 6/2017 |
| JP | 2018-514570 A | 6/2018 |
| KR | 10-2001-0039848 A | 7/2001 |
| KR | 10-2003-0003970 A | 1/2003 |
| KR | 10-2004-0098688 A | 11/2004 |
| KR | 10-2006-0059564 A | 6/2006 |
| KR | 10-2012-0062511 A | 6/2012 |
| KR | 10-2016-0064420 A | 6/2016 |
| RU | 2144945 C1 | 1/2000 |
| RU | 2229281 C1 | 5/2004 |
| WO | 93/00882 A1 | 1/1993 |
| WO | 93/08787 A2 | 5/1993 |
| WO | 94/08969 A1 | 4/1994 |
| WO | 94/08970 A1 | 4/1994 |
| WO | 95/01152 A1 | 1/1995 |
| WO | 95/01772 A1 | 1/1995 |
| WO | 95/15144 A1 | 6/1995 |
| WO | 96/15765 A1 | 5/1996 |
| WO | 97/24106 A1 | 7/1997 |
| WO | 98/56333 A1 | 12/1998 |
| WO | 99/11226 A1 | 3/1999 |
| WO | 99/66793 A1 | 12/1999 |
| WO | 01/35912 A1 | 5/2001 |
| WO | 01/47486 A1 | 7/2001 |
| WO | 01/52005 A1 | 7/2001 |
| WO | 02/19976 A1 | 3/2002 |
| WO | 02/32383 A2 | 4/2002 |
| WO | 02/32386 A2 | 4/2002 |
| WO | 02/055034 A2 | 7/2002 |
| WO | 2004/002411 A2 | 1/2004 |
| WO | 2004/019858 A2 | 3/2004 |
| WO | WO 2004/054525 | * 7/2004 |
| WO | 2005/058258 A1 | 6/2005 |
| WO | 2006/011771 A1 | 2/2006 |
| WO | 2006/134051 A1 | 12/2006 |
| WO | 2007/003307 A1 | 1/2007 |
| WO | 2007/038733 A1 | 4/2007 |
| WO | 2009/024936 A2 | 2/2009 |
| WO | 2010/015517 A2 | 2/2010 |
| WO | 2010/023559 A2 | 3/2010 |
| WO | 2010/049434 A2 | 5/2010 |
| WO | 2011/134785 A2 | 11/2011 |
| WO | 2011/146282 A2 | 11/2011 |
| WO | 2012/033813 A2 | 3/2012 |
| WO | 2012/080321 A2 | 6/2012 |
| WO | 2012/084532 A2 | 6/2012 |
| WO | 2012/084876 A2 | 6/2012 |
| WO | 2012/164064 A1 | 12/2012 |
| WO | 2013/071182 A1 | 5/2013 |
| WO | 2013/092080 A1 | 6/2013 |
| WO | 2013/136480 A1 | 9/2013 |
| WO | 2014/016407 A1 | 1/2014 |
| WO | 2014/072490 A1 | 5/2014 |
| WO | 2014/118212 A1 | 8/2014 |
| WO | 2014/125452 A1 | 8/2014 |
| WO | 2014/144076 A1 | 9/2014 |
| WO | 2014/167508 A1 | 10/2014 |
| WO | 2014/207097 A1 | 12/2014 |
| WO | 2015/017768 A1 | 2/2015 |
| WO | 2015/026994 A1 | 2/2015 |
| WO | 2015/033351 A1 | 3/2015 |
| WO | 2015/058942 A1 | 4/2015 |
| WO | 2015/069823 A1 | 5/2015 |
| WO | 2015/075064 A2 | 5/2015 |
| WO | 2015/118357 A2 | 8/2015 |
| WO | 2015/133382 A1 | 9/2015 |
| WO | 2015/175986 A2 | 11/2015 |
| WO | 2016/005114 A1 | 1/2016 |
| WO | 2016/005144 A1 | 1/2016 |
| WO | 2016/058749 A1 | 4/2016 |
| WO | 2016/069877 A1 | 5/2016 |
| WO | 2016/091492 A1 | 6/2016 |
| WO | 2016/098870 A1 | 6/2016 |
| WO | 2016/100885 A1 | 6/2016 |
| WO | 2016/102543 A1 | 6/2016 |
| WO | 2016/120642 A1 | 8/2016 |
| WO | 2016/161360 A1 | 10/2016 |
| WO | 2016/179017 A1 | 11/2016 |
| WO | 2015/198203 A1 | 12/2016 |
| WO | 2016207840 | 12/2016 |
| WO | 2017/041903 A1 | 3/2017 |
| WO | 2017/041905 A1 | 3/2017 |
| WO | 2017/041906 A1 | 3/2017 |
| WO | 2017/041907 A1 | 3/2017 |
| WO | 2017/041908 A1 | 3/2017 |
| WO | 2017/041909 A1 | 3/2017 |
| WO | 2017/041910 A1 | 3/2017 |
| WO | 2017/059646 A1 | 4/2017 |
| WO | 2017/085117 A1 | 5/2017 |
| WO | 2017/091794 A1 | 6/2017 |
| WO | 2017/091796 A1 | 6/2017 |
| WO | 2017/091797 A1 | 6/2017 |
| WO | 2017/091800 A1 | 6/2017 |
| WO | 2017/102855 A1 | 6/2017 |
| WO | 2017/102936 A1 | 6/2017 |
| WO | 2017/116465 A1 | 7/2017 |
| WO | 2017/196299 A1 | 11/2017 |
| WO | 2017/207198 A1 | 12/2017 |
| WO | 2018/081399 A1 | 5/2018 |
| WO | 2018/085478 A1 | 5/2018 |

OTHER PUBLICATIONS

Non-Final Office Action for copending U.S. Appl. No. 15/356,967, dated Dec. 30, 2022.
Third Party Submission for copending U.S. Appl. No. 17/694,821, dated Dec. 19, 2022.
Translation of Chinese Second Office Action for counterpart Application No. 201880021603.6, dated Dec. 8, 2021.

(56) References Cited

OTHER PUBLICATIONS

Non-Final Office Action for copending U.S. Appl. No. 15/339,035, dated Oct. 27, 2022.
Translation of Chinese Office Action for counterpart Application No. 2019800675489, dated Oct. 12, 2022.
Copending U.S. Appl. No. 15/484,625, filed Apr. 11, 2017.
Copending U.S. Appl. No. 15/484,663, filed Apr. 11, 2017.
Copending U.S. Appl. No. 15/339,035, filed Oct. 31, 2016.
PCT/US2016/03172 International Search Report and Written Opinion dated Sep. 19, 2016.
PCT/US2016/063724 International Search Report and Written Opinion dated Feb. 2, 2017.
PCT/US2016/063732 International Search Report and Written Opinion dated Feb. 6, 2017.
PCT/US2016/063728 International Search Report and Written Opinion dated Feb. 1, 2017.
Mintel: "Abundant Volume Conditioner," Alterna Professional Haircare, Database Record No. 2177147, Sep. 2013.
Mintel: "Hair Colourant," Catzy Hair Colourant, Database Record ID 743114, Jul. 2007, 4 pages.
Mintel: "Combing Cream," Devintex Cosmeticos, Database Record No. 1595490, Jul. 2011.
Mintel: "Combing Cream," Devintex Cosmeticos, Database Record No. 1595658, Jul. 2011.
Mintel: "Conditioner," Devintex Cosmeticos, Database Record No. 1595545, Jul. 2011.
Mintel: "Conditioner," Laperle Haircare, Database Record No. 3645337, Feb. 2016.
Mintel: "Conditioner," Laperle Haircare, Database Record No. 3790215, Feb. 2016.
Mintel: "Conditioner," Liqwd, Database Record No. 1172691, Sep. 2009.
Mintel: "Conditioner," TIGI, Database Record No. 1442418, Nov. 2010.
Mintel: "Conditioner," TIGI International, Database Record No. 1445427, Nov. 2010.
Mintel: "Conditioner," TGI International, Database Record No. 3280151, Jul. 2015.
Mintel, "Masque for Beautiful Color," Oribe Hair Care, Database Record No. 1522953, Mar. 2011.
Mintel: "Moisturizing Conditioner," Frederic Fekkai, Datablase Record No. 1507159, Mar. 2011.
Mintel: "Post-Service Perfector," Redken, Database Record No. 4326453, Nov. 2016.
Mintel: "Step 3—Conditioner," L'OREAL, Database Record No. 4353779, Oct. 2016.
Mintel: "Step 3—Conditioner," L'OREAL, Database Record No. 4609117, Feb. 2017.
International Preliminary Report on Patentability for PCT/US2016/30172, dated Jun. 19, 2017.
Non-Final Office Action for U.S. Appl. No. 15/484,625, dated Jun. 21, 2017.
Final Office Action for U.S. Appl. No. 15/484,625, dated Nov. 14, 2017.
Non-Final Office Action for U.S. Appl. No. 15/484,663, dated Jun. 21, 2017.
Final Office Action for U.S. Appl. No. 15/484,663, dated Nov. 28, 2017.
Non-Final Office Action for U.S. Appl. No. 15/339,035, dated Jan. 10, 2018.
International Search Report for PCT/US2017/058495, dated Jan. 5, 2018.
Third Party Submission for U.S. Appl. No. 15/484,663, filed Feb. 28, 2018 with attachments.
Pressly, Eric, et al., U.S. Appl. No. 61/994,709, filed May 16, 2014 and became publicly available on Nov. 19, 2015.
Estetica: the hairstyling professional magazine, (http://estetica.it/int/a/schwarzkopf-professional-launches-fibreplex), "Schwarzkopf Professional Launches Fibreplex," published Sep. 23, 2015 reporting that Fibreplex® was launched during Sep. 2015.
Fibreplex® No. 1 Product Label.
Fibreplex® No. 1 Material Safety Data Sheet.
International Preliminary Report on Patentability for counterpart Application No. PCT/US2016/063727, dated Jun. 7, 2018.
International Preliminary Report on Patentability for counterpart Application No. PCT/US2016/063732, dated Jun. 7, 2018.
International Preliminary Report on Patentability for counterpart Application No. PCT/US2016/063728, dated Jun. 7, 2018.
Non-Final Office Action for copending U.S. Appl. No. 15/484,625, dated Jun. 20, 2018.
International Preliminary Report on Patentability for counterpart Application No. PCT/US2016/063724, dated Jun. 7, 2018.
Non-Final Office Action for copending U.S. Appl. No. 15/339,035, dated Oct. 5, 2018.
Notice of Allowance for copending U.S. Appl. No. 15/484,625, dated Oct. 31, 2018.
Bayraktar, V.N., "Organic Acids Concentration in Wine Stocks After *Saccharomyces cerevisiae* Fermentation," Biotechnologia Acta, vol. 6, No. 2, Jan. 1, 2013, pp. 97-106.
Supplementary European Search Report for counterpart Application EP16789846, dated Oct. 30, 2018.
Communication Pursuant to Rules 70(32) and 70a(2) EPC for counterpart Application EP16789846, dated Jan. 23, 2019.
Written Opinion for counterpart Application EP16789846, dated Jan. 23, 2019.
Supplementary Extended Search Report and Written Opinion for counterpart European Application No. 16869324, dated Apr. 25, 2019.
Mintel: "Conditioner," Unilever, XP055576888, Database accession No. 1419415, Oct. 21, 2010.
Mintel: "Conditioner," Unilever, XP055576893, Database accession No. 3014885, Mar. 2, 2015.
Translation of Chinese Office Action for counterpart Application No. 201680079774.5, dated Sep. 1, 2020.
Fridman, R.A., "Technology of Cosmetics," publ. of "Food Industry," 1964, pp. 3-6, 297-308, 411-428 and 441-466.
Zefirova, N.S. "Big Russian Encyclopedia," Chemical Encyclopedia, 1995, vol. 4, pp. 183-185.
Third Party Submission for U.S. Appl. No. 16/712,326, filed Sep. 8, 2020 with attachments.
Mexican Office Action for counterpart Application No. MX/a/2017/013983, dated Sep. 15, 2020.
Non-Final Office Action for copending U.S. Appl. No. 16/176,350, dated Sep. 30, 2020.
Non-Final Office Action for copending U.S. Appl. No. 15/778,807, dated Oct. 9, 2020.
Japanese Notice of Reasons for Refusal for counterpart Application No. 2019-553190, dated Oct. 27, 2020.
Translation of Korean Notice of Last Preliminary Rejection for counterpart Application No. 10-2018-7017668, dated Oct. 21, 2020.
Non-Final Office Action for copending U.S. Appl. No. 15/942,042, dated Nov. 12, 2020.
Final Office Action for copending U.S. Appl. No. 15/356,967, dated Nov. 17, 2020.
Final Office Action for copending U.S. Appl. No. 15/357,056, dated Nov. 19, 2020.
Japanese Office Action for counterpart Application No. 2018-546408, dated Dec. 7, 2020.
Japanese Notice of Reasons for Rejection for counterpart Application No. 2019-553559, dated Dec. 1, 2020.
Japanese Notice of Reasons for Rejection for counterpart Application No. 2019-564945, dated Dec. 1, 2020.
Final Office Action for copending U.S. Appl. No. 16/234,883, dated Dec. 24, 2020.
Translation of Third Party Observation for Application No. 2018-546408, dated Sep. 11, 2020.
European Office Action for counterpart Application No. 16869327.3-1112, dated Dec. 18, 2020.
Translation of Russian Office Action for counterpart Application No. 2018114758/04, dated Dec. 21, 2020.
Non-Final Office Action for copending Application No. 16/455,139, dated Jan. 26, 2021.

(56) References Cited

OTHER PUBLICATIONS

Chinese Office Action for counterpart Application No. 201680039105.5, dated Feb. 4, 2021.
European Office Action for counterpart Application No. 16869330.7-1112, dated Feb. 4, 2021.
European Office Action for counterpart Application No. 16869324.0-1112, dated Feb. 18, 2021.
Translation of Chinese Office Action for counterpart Application No. 201680079800.4, dated Feb. 24, 2021.
Translation of Chinese Office Action for counterpart Application No. 201880021603.6, dated Mar. 2, 2021.
Final Office Action for copending U.S. Appl. No. 15/941,916, mailed Mar. 10, 2021.
Final Office Action for copending U.S. Appl. No. 15/941,965, mailed Apr. 5, 2021.
Supplemental Search Report for Chinese Application No. 201680079800.4, dated Feb. 18, 2021.
Partial Translation of Office Action for copending MX Application No. MX/a/2017/013983, dated Apr. 4, 2021.
Translation of Chinese Office Action for counterpart Application 201680079773, dated Apr. 14, 2021.
Chinese Office Action for counterpart Application No. 201680079110.9, dated Apr. 26, 2021.
Final Office Action for copending U.S. Appl. No. 15/942,042, dated May 12, 2021.
Translation of Japanese Office Action for counterpart Application No. 2017-557074, dated May 31, 2021.
Non-Final Office Action for copending U.S. Appl. No. 15/942,085, dated Jun. 8, 2021.
Tetrasodium Etidronate, https://uk.lush.com/ingredients/tetrasodium-etidronate. Published Mar. 28, 2020.
Shoup, F.K. et al., "Amino Acid Composition of Wheat Varieties and Flours Varying Widely in Bread-Making Potentialities," Journal of Food Science, vol. 31, Issue 1, published Jan. 1966, pp. 94-101.
"Oxy Cream," Makki Cosmetics, https://www.makkicosmetics.com/makki/showProduct.jsp?productID=Oxy25030&brandID=Makki, published: Jun. 30, 2016.
Non-Final Office Action for copending U.S. Appl. No. 15/339,035, dated Jun. 25, 2021.
Non-Final Office Action for copending U.S. Appl. No. 15/603,889, dated Jun. 25, 2021.
Japanese Notice of Reasons for Refusal for counterpart Application No. 2019-553190, dated Jun. 12, 2021.
Final Office Action for copending U.S. Appl. No. 15/778,807, dated Jul. 21, 2021.
Non-Final Office Action for copending U.S. Appl. No. 15/356,967, dated Jul. 22, 2021.
Translated Russian Office Action for counterpart Application No. 2018114758/04(023100), dated Jul. 20, 2021.
Chinese Office Action for counterpart Application No. 201680079110.9, dated Aug. 5, 2021.
Copending U.S. Appl. No. 17/228,040, Titled: "Compositions for Altering the Color of Hair," Inventors: Kimberly Dreher et al., filed Apr. 12, 2021.
Copending U.S. Appl. No. 17/403,327, Titled: "Hair Treatment Compositions, Methods, and Kits for Treating Hair," Inventors: Barbara Mitchell et al., filed Aug. 16, 2021.
Final Office Action for copending U.S. Appl. No. 16/455,139, dated Aug. 11, 2021.
Non-Final Office Action for copending U.S. Appl. No. 16/234,883, dated Sep. 17, 2021.
Final Office Action for copending U.S. Appl. No. 15/942,085, dated Sep. 21, 2021.
Chinese Office Action for counterpart Application No. 201880021603.6, dated Dec. 8, 2021.
Chinese Office Action for counterpart Application No. 201880034065.4, dated Dec. 22, 2021.
Final Office Action for copending U.S. Appl. No. 15/603,889, dated Jan. 6, 2022.
Translation of Chinese Office Action for counterpart Application No. 201680039105.5, dated Jan. 14, 2022.
Translation of Chinese Office Action for counterpart Application No. 201880034056.6, dated Dec. 28, 2021.
Translation of Japanese Notice of Reasons for Refusal for counterpart JP Application No. 2021-071866, dated Mar. 28, 2022.
Extended European Search Report for counterpart EP Application No. 21204522.3-1112, dated Mar. 30, 2022.
Final Office Action for copending U.S. Appl. No. 15/356,967, dated Mar. 31, 2022.
Final Office Action for copending U.S. Appl. No. 16/234,883, dated Apr. 12, 2022.
Final Office Action for copending U.S. Appl. No. 15/339,035, dated Apr. 14, 2022.
Japanese Notice of Opposition for Japanese Patent No. 6,930,994, dated Mar. 28, 2022 (no translation available).
Third Party Submission for counterpart Application No. EP 20160869327, dated Apr. 22, 2022.
Communication Pursuant to Rule 114(2) EPC (Third Party Observation) for EP Application No. 20160869324, dated Apr. 22, 2022.
U.S. Appl. No. 61/994,709 for "Hair Treatment Compositions and Methods," Inventors: Eric D. Pressly and Craig J. Hawker, filed May 16, 2014.
"Practical Modern Hair Science," Chapter 4, Edited by Trefor Evans and R. Randall Wickett, Allured Business Media, 2012, pp. 1065-1-1065-45.
Third Party Submission and Concise Description of Relevance for U.S. Application No. 17/356, 132, dated Apr. 20, 2022.
First Office Action for counterpart Chinese Application No. 201880084390.1, dated Jun. 30, 2022.
Third Party Submission for counterpart Application No. EP 20160869330, dated May 6, 2022.
Third Party Submission for copending U.S. Appl. No. 17/379,405, filed May 10, 2022.
Non-Final Office Action for copending U.S. Appl. No. 15/942,042, dated May 23, 2022.
Translation of Second Chinese Office Action for counterpart Application No. 201880034056.5, dated May 30, 2022.
European Office Action for counterpart Application No. 16789846.9-1109, dated Jul. 6, 2022, translation.
Third Party Submission and Concise Description of Relevance for copending U.S. Appl. No. 17/403,327, dated Jun. 27, 2022.
Korean Notice of Final Rejection for counterpart KR Application No. 10-2021-7019867, dated Jul. 22, 2022, translation.
Third Party Submission for copending U.S. Appl. No. 17/356,131, dated Apr. 20, 2022.
International Preliminary Report on Patentability for counterpart Application No. PCT/US2018/025418, dated Oct. 1, 2019.
Notice of Allowance for copending U.S. Appl. No. 15/604,152, dated Oct. 2, 2019 (now U.S. Pat. No. 10,561,599).
Non-Final Office Action for copending U.S. Appl. No. 15/604,152, dated Jun. 13, 2019.
Olaplex with relaxers, OLAPEX™, pp. 1-2, Apr. 11, 2017, https://olaplex.es/olaplex-with-relaxers/.
Relaxers, resource Library, Olaplex Education, pp. 1-2, Apr. 11, 2017, https://help.olaplex.com/detail/relaxers.
Notice of Allowability for copending U.S. Appl. No. 15/604,152, dated Dec. 10, 2019.
International Search Report and Written Opinion for counterpart Application No. PCT/US2018/034366, dated Jul. 25, 2018.
Anonymous: "Curly Hair Conditioner," Mintel, GNPD, XP002742449, 2015, pp. 1-2.
Corrected Notice of Allowability for copending U.S. Appl. No. 15/604,189, dated Dec. 11, 2019 (now U.S. Pat. No. 10,576,307).
Notice of Allowance for copending U.S. Appl. No. 15/604,189, dated Oct. 22, 2019.
Non-Final Office Action for copending U.S. Appl. No. 15/604,189, dated Apr. 8, 2019.
International Search Report and Written Opinion for counterpart Application No. PCT/US2018/034371, dated Nov. 16, 2018.
Mintel: "Hydrating Hair Colour," Garnier, Jan. 2017, pp. 1-6.
Mintel: "Masque Force Architecte Reconstructing Masque," L'Oreal, Feb. 2012, pp. 1-6.

(56) References Cited

OTHER PUBLICATIONS

Final Office Action for copending U.S. Appl. No. 15/603,889, dated Jul. 12, 2019.
Non-Final Office Action for copending U.S. Appl. No. 15/603,889, dated Jan. 2, 2019.
International Search Report and Written Opinion for counterpart Application No. PCT/US2018/034378, dated Jul. 24, 2018.
Final Office Action for copending U.S. Appl. No. 16/234,883, dated Mar. 11, 2020.
Non-Final Office Action for copending U.S. Appl. No. 16/234,883, dated Sep. 16, 2019.
International Search Report and Written Opinion for counterpart Application No. PCT/US2018/067814, dated Feb. 25, 2019.
Final Office Action for copending U.S. Appl. No. 16/176,350, dated Apr. 8, 2020.
Non-Final Office Action for copending U.S. Appl. No. 16/176,350, dated Nov. 14, 2019.
International Search Report and Written Opinion for counterpart Application No. PCT/US2019/059002, dated Feb. 4, 2020.
Korean Notification of Reason for Refusal for counterpart Application No. KR10-2017-7034789, dated May 19, 2020 (translation).
Final Office Action for copending U.S. Appl. No. 15/942,042, dated Jun. 1, 2020.
JP Notice of Reasons for Refusal for Application No. 2017-557074, dated Jun. 1, 2020.
Non-Final Office Action for copending U.S. Appl. No. 15/942,085, dated Jun. 19, 2020.
Shiseido Super Mild Hair Care-Shampoo & Conditioner Refill Set. Https://web.archive.org/web/20160326190615/http://www.truenu.com/TR/Shiseido-Super-Mild-Hair-Care-Shampoo-Conditioner-Refill-Set-Two-400ml-Refill-Pouches-Details.html. Published Mar. 26, 2016.
Non-Final Office Action for copending U.S. Appl. No. 15/941,916, dated Jun. 24, 2020.
Non-Final Office Action for copending U.S. Appl. No. 15/941,965, dated Jul. 15, 2020.
Third Party Observation for counterpart Application No. EP20160869330, dated Jun. 26, 2020.
Translation of Japanese Office Action for counterpart Application No. 2018-526844, dated Aug. 3, 2020.
Translation of Chinese Office Action for counterpart Application No. 201680079110.9, dated Aug. 11, 2020.
Ruiming, Li, "Hairdressing Technology," China Railway Publishing House, Jun. 30, 2015, pp. 112-113.
Translation of Mexican Office Action for counterpart Application No. MX/a/2018/005829, dated Jul. 13, 2020.
Non-Final Office Action for copending U.S. Appl. No. 16/234,883, dated Aug. 26, 2020.
Mascolo Group, label.m Anti-Frizz Mist, MINTEL GNPD, record ID5618119, published Apr. 2018, p. 1-5.
Federici Brands, Color WOW Dream Coat Supernatural Spray, MINTEL GNPD, record ID5637153, published Apr. 2018, p. 1-2.
Garnier, Garnier Fructis Sleek & Shine Moroccan Sleek Oil Treatment, MINTEL GNPD, record ID1876023, published Sep. 2012, p. 1-2.
Ouai, Leave-In Conditioner, Mintel Gnpd, record ID5781323, published Jun. 2018, p. 1-2.
Redken, Redken Pillow Proof Express Treatment Primer, MINTEL GNPD, record ID5117339, published Sep. 2017, p. 1-4.
Redken, Redken Pillow Proof Express Primer Time-Saving Blowdry Primer with Heat Protection, MINTEL GNPD, record ID6117357, published Nov. 2018, p. 1-2.
Redken, Redken Pillow Proof Time-Saving Blowdry Primer with Heat Protection, MINTEL GNPD, record ID4537755, published Jan. 2017, p. 1-3.
Copending U.S. Appl. No. 16/455,139, "Hair Treatment Compositions and Methods for Treating Hair," filed Jun. 27, 2019.
Translation of Russian Office Action for counterpart Application No. 2017134681-04, dated Aug. 17, 2020.
Translation of Chinese Office Action for counterpart Application No. 201680079800.4, dated Aug. 24, 2020.
Search Report for counterpart Chinese Application No. 201680079800.4, dated Aug. 24, 2020.
Translation of Chinese Office Action for counterpart Application No. 201680079773.0, dated Aug. 21, 2020.
Search Report for counterpart Chinese Application No. 201680079773.0, dated Aug. 21, 2020.
Translation of Japanese Office Action for counterpart Application No. 2018-546409, dated Sep. 7, 2020.
1 Non-Final Office Action for copending U.S. Appl. No. 17/694,821, dated Apr. 14, 2023.
"Olaplex Alleges Patent Infringement by L'OREAL re Hairbond-Building Prior to Colouring," Focus on Pigments, vol. 2017, No. 3, Mar. 31, 2017, p. 7.
Final Office Action for co-pending U.S. Appl. No. 15/339,035, dated May 2, 2019.
International Preliminary Report on Patentability for counterpart Application No. PCT/US2017/058495 dated May 9, 2019.
Notice of Allowance for copending U.S. Appl. No. 15/778,803, dated Jun. 3, 2019.
Extended European Search Report for counterpart Application No. 16869327.3-1114, dated Jun. 4, 2019.
Mintel: "Detox 7 Day Cure Purifying Serum," XP055593471, Jeanne Gatineau, Feb. 11, 2013.
Extended European Search Report for counterpart Application No. 16869330.7-1114, dated Jul. 5, 2019.
Extended European Search Report for counterpart Application No. 16869326.5-1114 dated Jun. 26, 2019.
Translation of Mexican Office Action for counterpart Application No. MX/a/2018/005829, dated Jun. 13, 2019.
Non-Final Office Action for co-pending U.S. Appl. No. 15/339,035, dated Aug. 20, 2019.
Mexican Office Action for counterpart Application No. MX/a/2017/013983, dated Jul. 2, 2019.
Notice of Allowance for co-pending U.S. Appl. No. 16/042,478, dated Sep. 25, 2019.
Non-Final Office Action for co-pending U.S. Appl. No. 15/778,807, dated Sep. 30, 2019.
Brazilian Office Action for counterpart Application No. BR112017023380-0, dated Oct. 10, 2019.
Brazilian Office Action for counterpart Application No. BR112018010381-0, dated Nov. 25, 2019.
Brazilian Office Action for counterpart Application No. BR112018010357-8, dated Nov. 25, 2019.
Mexican Office Action for counterpart Application No. MX/a/2018/005829, dated Oct. 5, 2019.
Brazilian Office Action for counterpart Application No. BR112018010344, dated Nov. 25, 2019.
Mexican Office Action for counterpart Application No. MX/a/2017/013983, dated Dec. 16, 2019.
Japanese Office Action for counterpart Application No. 2018-526844, dated Dec. 23, 2019.
Japanese Office Action for counterpart Application No. 2018-546409, dated Dec. 23, 2019.
Brazilian Written Opinion for counterpart Application No. BR112018010341, dated Nov. 25, 2019.
Non-Final Office Action for counterpart Japanese Application No. 2018-546408, dated Jan. 6, 2020.
Mintel: "Tonic," Dr. Kurt Wolff, Dr. Wolff Plantur 39, ID# 3133037, Apr. 2015.
Mintel: "Conditioner," LG Household & Health Care, Beyond Professional, ID# 3240637, Jun. 2015.
Russian Office Action for counterpart Application No. 2018114758/04, dated Dec. 13, 2019.
Translated Notification of Reasons for Refusal for counterpart KR Application No. 10-2018-7017668, dated Jan. 21, 2020.
Translated Office Action for counterpart RU Application No. 2017134681/04(0060925), dated Dec. 30, 2019.
Non-Final Office Action for copending U.S. Appl. No. 15/778,805, dated Feb. 12, 2020.
Final Office Action for copending U.S. Appl. No. 15/778,807, dated Mar. 13, 2020.

(56) References Cited

OTHER PUBLICATIONS

Final Office Action for copending U.S. Appl. No. 15/339,035, dated Apr. 10, 2020.
Non-Final Office Action for copending U.S. Appl. No. 16/273,787, dated Apr. 9, 2020.
International Search Report and Written Opinion for counterpart Application No. PCT/US2017/059827, dated Jun. 28, 2018.
"LAMESOFT PO 65 Datasheet," Retrieved from the internet on Jun. 7, 2018, http://e-applications.basf-ag.de/data/basf-pcan/pds2/pds2-web.nsf.
Non-Final Office Action for copending U.S. Appl. No. 15/356,967, dated May 3, 2017.
Final Office Action for copending U.S. Appl. No. 15/356,967, dated Dec. 4, 2017.
Non-Final Office Action for copending U.S. Appl. No. 15/356,967, dated Aug. 24, 2018.
Final Office Action for copending U.S. Appl. No. 15/356,967, dated Apr. 11, 2019.
Non-Final Office Action for copending U.S. Appl. No. 15/356,967, dated Feb. 21, 2020.
International Search Report and Written Opinion for counterpart Application No. PCT/US2017/059817, dated Feb. 6, 2018.
Non-Final Office Action for copending U.S. Appl. No. 15/357,056, dated Apr. 16, 2020.
Non-Final Office Action for copending U.S. Appl. No. 15/942,042, dated Jan. 24, 2020.
ALS "Cocamidopropyl betaine," printed 2020; http://www.caslab.com/Cocamidopropyl_betaine_CAS_61789-40-0.
International Search Report and Written Opinion for counterpart Application No. PCT/US2018/025466, dated Jul. 9, 2018.
International Preliminary Report on Patentability for counterpart Application No. PCT/US2018/025466, dated Oct. 1, 2019.
International Search Report and Written Opinion for counterpart Application No. PCT/US2018/025448, dated Jul. 9, 2018.
International Preliminary Report on Patentability for counterpart Application No. PCT/US2018/025448, dated Oct. 1, 2019.
International Search Report and Written Opinion for counterpart Application No. PCT/US2018/025431, dated Jun. 20, 2018.
International Preliminary Report on Patentability for counterpart Application No. PCT/US2018/025431, dated Oct. 1, 2019.
Translation of Brazilian Office Action for counterpart Application No. BR112021006046-4, dated May 2, 2023.
Translation of Chinese Office Action for counterpart Application No. CN202110948497.X, dated Apr. 26, 2023.
Non-Final Office Action for copending U.S. Appl. No. 17/531,407, dated Jul. 6, 2023.
Final Office Action for copending U.S. Appl. No. 15/941,965, mailed Jul. 3, 2023.
"Bigen Speedy Hair Color Conditioner-Natural Black 881," Aug. 5, 2013, https://www.cosdna.com/chs/cosmetic-8836116377.html.
Second Chinese Office Action for counterpart Application No. 201980067548.9, dated Jul. 12, 2023 (translation unavailable).

* cited by examiner

HAIR TREATMENT COMPOSITIONS, METHODS, AND KITS FOR TREATING HAIR

CROSS REFERENCE TO RELATED APPLICATION

This is a continuation of U.S. application Ser. No. 16/176,350 filed on Oct. 31, 2018, which is incorporated herein by reference in its entirety.

FIELD OF THE DISCLOSURE

The instant disclosure relates to hair treatment compositions that are particularly useful for improving the quality of hair. Also disclosed are kits that include the hair treatment compositions and methods for using the hair treatment compositions.

BACKGROUND

Many consumers desire to use cosmetic and care compositions that enhance the appearance of keratinous substrates such as hair, e.g., by changing the color, style, and/or shape of the hair, and/or by imparting various cosmetic properties to hair, such as shine and conditioning. Many of the known compositions and processes for enhancing the appearance of hair involve chemical treatments to the hair.

The process of changing the color of hair, for example, can involve depositing an artificial color onto the hair which provides a different shade or color to the hair, and/or lifting the color of the hair, such as lightening the color of dark hair to lighter shades. The process of lifting the color of hair, also known as lightening (or bleaching), generally requires the use of oxidizing agents. Lightening of hair is typically evaluated by the variation in tone height before and after the application of a hair color-altering composition onto hair. This variation corresponds to the degree or level of lightening or lift. The notion of "tone" is based on the classification of the natural shades, one tone separating each shade from the shade immediately following or preceding it, which is well known to hairstyling professionals. The tone heights or levels can range from 1 (black) to 10 (light blond), one unit corresponding to one tone; thus, the higher the number, the lighter the shade or the greater the degree of lift.

Additionally, there are many techniques and compositions for styling or altering the shape of hair. For example, hair care products referred to as "hair relaxers" or "hair straighteners" can relax or straighten curly or kinky hair, including wavy hair. Straightening or relaxing the curls of very curly hair may increase the manageability and ease of styling of such hair. Compositions for permanent waving the hair will impart a curl or a wave to otherwise straight hair. Different types of compositions can be applied onto hair in order to change its shape and make it more manageable, such as alkaline and acidic compositions. Hair relaxers, straighteners, perms, and/or waves may either be applied in a hair salon by a professional or in the home by the individual consumer.

While dyeing or color lifting compositions can effectively alter the color of hair, and relaxing, straightening, perming, and waving compositions can effectively alter the shape of the hair, these chemical treatments can damage the hair fibers and/or irritate the scalp. Thus, in order to reduce or avoid damage to hair, as well as to improve the cosmetic performance of the compositions, the use of new and additional components and novel combinations of ingredients are continuously sought.

However, the choice of components or combinations of ingredients could pose difficulties insofar as they cannot be detrimental to other cosmetic attributes such as ease and uniformity of application, rheology or viscosity properties and stability of the compositions, color deposit and target shade formation, and/or result into more disadvantages such as increased damage or a less healthy look to the hair. It would therefore be desirable to provide the consumer with compositions and methods that can chemically treat the hair while providing other cosmetic advantages such as shine, conditioning, fiber strength, and/or a healthy appearance to the hair, but avoiding or minimizing damage to the hair.

Further, both natural and sensitized or chemically treated hair can contain several kinds of negatively charged moieties, for example, carboxylates (resulting from the hydrolysis of amino acids and thioester bonds) and/or sulfonates (resulting from the oxidation of disulfide bonds). These negatively charged moieties can degrade the cosmetic properties of the hair. Moreover, when hair is chemically treated or damaged, the disulfide bonds in hair (disulfide linkages between two cysteine units) can be reduced or broken, resulting in the formation of thiol groups and/or cysteic acid. There is therefore an ongoing need for hair treatment compositions which help to improve the properties of hair.

SUMMARY OF THE DISCLOSURE

One aspect of the invention pertains to a hair treatment composition comprising:
- at least 0.5 wt. % of at least one non-polymeric mono, di, or tricarboxylic acid, and/or a salt thereof;
- one or more amines selected from the group consisting of diamines, polyamines, alkylamines, alkanolamines, and a mixture thereof;
- one or more fructan polysaccharides;
- one or more prosolvents; and
- water.

In one or more embodiments, the at least one non-polymeric mono, di, or tricarboxylic acid, and/or a salt thereof, is a dicarboxylic acid and/or a salt thereof. In some embodiments, wherein the composition comprises at least one dicarboxylic acid and/or a salt thereof, and the at least one dicarboxylic acid and/or a salt thereof is selected from the group consisting of oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, and a salt thereof. In one or more embodiments, the at least one dicarboxylic acid and/or a salt thereof is maleic acid, malonic acid, and/or a salt thereof. In some embodiments, the composition comprises at least one tricarboxylic acid and/or a salt thereof, and the at least one tricarboxylic acid and/or a salt thereof is selected from the group consisting of citric acid, isocitric acid, aconitric acid, propane-1,2,3-tricarboxylic acid, benzene-1,3,5-tricarboxylic acid, and a thereof. In one or more embodiments, the at least one tricarboxylic acid and/or a salt thereof is citric acid, and/or a salt thereof. In some embodiments, the composition comprises at least 0.5 to about 20 wt. % of at least one non-polymeric mono, di, or tricarboxylic acid and/or a salt thereof, based on the total weight of the hair treatment composition. In one or more embodiments, the composition comprises one or more alkylamines and/or alkanolamines selected from the group consisting of compounds of formula (II):

$NR_3R_4R_5$ (II)

wherein $R_3$, $R_4$ and $R_5$ are independently H, $C_1$-$C_{40}$ alkyl, $C_1$-$C_{40}$ monohydroxyalkyl or $C_2$-$C_{40}$ polyhydroxyalkyl, provided that at least one of $R_3$, $R_4$ and $R_5$ is an alkyl or mono or polyhydroxyalkyl. In some embodiments, the composition comprises one or more alkanolamines selected from the group consisting of monoethanolamine, diethanolamine, triethanolamine, monoisopropanolamine, diisopropanolamine, N-dimethylamino-ethanolamine, 2-amino-2-methyl-1-propanol, triisopropanolamine, 2-amino-2-methyl-1,3-propanediol, 3-amino-1,2-propanediol, 3-dimethylamino-1,2-propanediol, tris(hydroxymethylamino)methane, and a mixture thereof. In one or more embodiments, the composition comprises monoethanolamine. In some embodiments, the total amount of the one or more amines is about 1 to about 20 wt. %, based on the total weight of the hair treatment composition. In one or more embodiments, the one or more fructan polysaccharides are inulin polysaccharides and/or levan polysaccharides. In some embodiments, the one or more fructan polysaccharides comprises inulin. In some embodiments, the one or more fructan polysaccharides are present in an amount from about 1 to about 5 wt. %, based on the total weight of the hair treatment composition. In one or more embodiments, the one or more prosolvents is selected from the group consisting of hexylene glycol, butylene glycol, propylene glycol, and combinations thereof.

Any of the above embodiments may be combined. For example, in some embodiments, the hair treatment composition comprises:
  about 2 to about 4 wt. % of maleic acid and/or a salt thereof;
  about 1 to about 3 wt. % of ethanolamine;
  about 1 to about 5 wt. % inulin;
  about 2 to about 4 wt. % of a mixture of hexylene glycol and butylene glycol; and
  water.

Another aspect of the invention pertains to methods of treating hair. In some embodiments, the method comprises applying any of the compositions described herein to hair. In one or more embodiments, the composition is applied to hair as part of a shampoo or conditioning routine. In some embodiments, the composition is applied after a chemical relaxer is applied to the hair.

DETAILED DESCRIPTION OF THE DISCLOSURE

The term "hair treatment composition" encompasses many types of compositions for application to the hair, for example, chemical relaxer compositions, shampoos, conditioners, hair-rinses, hair lotions, hair gels, mouse-type products, sprays, etc. A hair treatment composition is characterized by its ability to provide a cosmetic benefit to the hair. As is well-known, a shampoo provides cleansing benefits to the hair, a conditioner provides conditioning benefits to the hair, and gels can provide styling benefits to the hair. Non-limiting examples of additional benefits that can be imparted to hair include strength, smoothness, softness, and suppleness.

The hair treatment compositions of the instant disclosure typically include:
  at least 0.5 wt. % of at least one non-polymeric mono, di, or tricarboxylic acid, and/or a salt thereof;
  one or more amines selected from the group consisting of diamines, polyamines, alkylamines, alkanolamines, and a mixture thereof;
  one or more fructan polysaccharides;
  one or more prosolvents; and
  water.

The above compositions, which feature a unique combinations of ingredients, advantageously provide hair strengthening benefits together with styling benefits.

The hair treatment compositions described herein may be in any suitable physical form. Suitable forms include, but are not limited to low to moderate viscosity liquids, lotions, milks, mousses, sprays, gels, creams, pastes, clays, bars, conditioners, and the like. For instance, spray formulations may be dispensed from containers that include aerosol dispensers or pump spray dispensers. Such dispensers are known in the art and are commercially available from a variety of manufacturers. When the spray formulation is dispensed from a pressurized aerosol container, a propellant may be used to force the composition out of the container. Suitable propellants include, but are not limited to, a liquefiable gas or a halogenated propellant. Examples of suitable propellants include dimethyl ether and hydrocarbon propellants such as propane, n-butane, iso-butane, CFCs, and CFC-replacement propellants. The propellants may be used singly or admixed. Furthermore, the leave-on hair styling compositions may be in the form of an emulsion (e.g., water-in-oil or oil-in-water emulsion). In some cases, the leave-in hair styling composition is in the form of a paste, which may be a semi-solid product that can be applied throughout the hair using one's fingers.

The hair treatment compositions may be packaged in a variety of different containers, such as, for example, a ready-to-use container. Non-limiting examples of useful packaging include tubes, jars, caps, unit dose packages, and bottles, including squeezable tubes and bottles.

Non-Polymeric Mono, Di, Or Tricarboxylic Acid

A non-polymeric mono, di, and/or tricarboxylic acid is an organic compound having one (mono), two (di), or three (tri) carboxylic acid groups (—COOH). The non-polymeric mono, di, and tricarboxylic acids, and/or salts thereof, typically have a molecular weight of less than about 500 g/mol, less than about 400 g/mol, or less than about 300 g/mol.

Non-limiting examples of monocarboxylic acids, or salts thereof, include formic acid, acetic acid, propionic acid, butyric acid, valeric acid, caproic acid, entanthic acid, caprylic acid, pelargonic acid, capric acid, undecylic acid, lauric acid, tridecylic acid, lauric acid, tridecylic acid, myristic acid, pentadecylic acid, palmitic acid, margaric acid, stearic acid, nonadecylic acid, arachidic acid, lactic acid, a salt thereof, and a mixture thereof. In some cases, the hair treatment compositions include at least lactic acid and/or a salt thereof.

Non-limiting examples of dicarboxylic acids and/or salts thereof include oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, a salt thereof, and a mixture thereof. In some cases, the hair treatment compositions include oxalic acid, malonic acid, malic acid, maleic acid, a salt thereof, or a mixture thereof.

Non-limiting examples of tricarboxylic acids and salts thereof include citric acid, isocitric acid, aconitric acid, propane-1,2,3-tricarboxylic acid, benzene-1,3,5-tricarboxylic acid, a salt thereof, and a mixture thereof. In some instances, the hair treatment compositions include at least citric acid and/or a salt thereof.

In some cases, the hair treatment compositions include at least one or more dicaboxylic acids, and/or a salt thereof, in particular, oxalic acid, malonic acid, malic acid, maleic acid, a salt thereof, or a mixture thereof. A particularly useful dicarboxylic acid is malonic acid and/or a salt thereof.

The total amount of the at least one non-polymeric mono, di, or tricarboxylic acid, and/or a salt thereof, is at least 0.5 wt. %, based on the total weight of the hair treatment composition. In some cases, the total amount of the at least one non-polymeric mono, di, or tricarboxylic acid, and/or salt thereof, is at least 0.6, 0.7, 0.8, 0.9, or 1 wt. % up to about 15, 20, 25, or 30 wt. %. Furthermore, the total amount of the at least one non-polymeric mono, di, or tricarboxylic acid, and/or salt thereof, may be at least 0.5 wt. % to about 50 wt. %, at least 0.5 wt. % to about 40 wt. %, at least 0.5 wt. % to about 30 wt. %, at least 0.5 wt. % to about 20 wt. %, at least 0.5 wt. % to about 10 wt. %, at least 0.5 wt. % to about 5 wt. %, at least 0.8 wt. % to about 50 wt. %, at least 0.8 wt. % to about 40 wt. %, at least 0.8 wt. % to about 30 wt. %, about 0.8 to about 20 wt. %, about 0.8 to about 10 wt. %, about 0.8 wt. % to about 5 wt. %, about 1 wt. % to about 50 wt. %, about wt. % to about 40 wt. %, about 1 wt. % to about 30 wt. %, about 1 wt. % to about 20 wt. %, about 1 wt. % to about 10 wt. %, about 1 wt. % to about 5 wt. %, about 2 wt. % to about 50 wt. %, about 2 wt. % to about 40 wt. %, about 2 wt. % to about 30 wt. %, about 2 wt. % to about 20 wt. %, about 2 wt. % to about 10 wt. %, or about 2 wt. % to about 5 wt. %.

Amines

Non-limiting examples of the types of amines that may be used in the hair treatment compositions are vast, but may include diamines, polyamines, alkylamines, alkanolamines, and mixtures thereof. The one or more amines may be primary, secondary, tertiary amines, and mixtures thereof.

Diamines

Non-limiting examples of diamines that may be useful may be primary amines and secondary amines. The diamine can include both primary and secondary amine groups. Optional diamines may include at least one ethylene oxide group. For example, between 1 and 4 ethylene oxide groups can be present in the diamine. The diamine may optionally include propylene oxide groups. For example, between 1 and 4 propylene oxide groups can be present in the diamine. Non-limiting examples of diamines include 4,9-dioxadodecane-diamine; 4,7,10-trioxa-1,13-tridecanediamine; ethylenediamino; polyoxypropylene diamine; polyethylene glycol diamine; triethylene glycol diamine (2OE); n-(2-hydroxyethyl)-ethylenediamine; 1,3-diaminopropane; 1,7-diaminoheptane; 1,4-diaminobutane; 1,2-diaminopropane; 1,6-diaminohexane; 1,11-diamino-3,6,9-trioxaundecane; 1,5-diaminopentane; polyoxyethylene diamine; 2,2-dimethyl-1,3-propanediamine; 2,2-bis(aminoethoxy)propane; 4,7,10-trioxa-1,13-tridecanediamine; 1,3-diaminopentane; 4,7,10-trioxa-1,13; 1,5-diamino-2-methylpentane; (3s,4s)-(−)-3,4-hexanediamine dihydrochloride; 1,9-diaminononane, and mixtures thereof.

In some cases, diamines may be selected from the group consisting of 4,9-dioxadodecane-diamine, 4,7,10-trioxa-1, 13-tridecanediamine, ethylenediamino, polyoxypropylene diamine, polyethylene glycol diamine, triethylene glycol diamine (2OE); n-(2-hydroxyethyl)-ethylenediamine; 1,3-diaminopropane, 1,7-diaminoheptane, 1,4-diaminobutane, 1,2-diaminopropane, 1,6-diaminohexane, 1,11-diamino-3,6, 9-trioxaundecane, 1,5-diaminopentane, polyoxyethylene diamine, 2,2-dimethyl-1,3-propanediamine, 2,2-bis(aminoethoxy)propane, 4,7,10-trioxa-1,13-tridecanediamine, 1,3-diaminopentane, 4,7,10-trioxa-1,13; 1,5-diamino-2-methylpentane, (3s,4s)-(−)-3,4-hexanediamine dihydrochloride, 1,9-diaminononane, and mixtures thereof.

Polyamines

Polyamines have more than two amino groups. In some cases, the composition of the instant disclosure may include one or more polyamines, but in some cases, the compositions are free or essentially free of polyamines. The polyamine may be, for example, aminated polysaccharides comprising multiple amino groups, such as, for example, hydrolysates of aminated polysaccharides.

The polyamine may also be a polymer comprising multiple amino groups including homopolymers, copolymers, and terpolymers.

In some cases, polyamines are chosen from polyethyleneimines. Polyethyleneimines may optionally be substituted. Non-limiting examples of polyethyleneimines which may be used include LUPASOL products commercially available from BASF. Suitable examples of LUPASOL polyethyleneimines include LUPASOL PS, LUPASOL PL, LUPASOL PR8515, LUPASOL G20, LUPASOL G35 as well as LUPASOL SC Polythyleneimine Reaction Products (such as LUPASOL SC-61B, LUPASOL SC-62J, and LUPASOL SC-86X). Other non-limiting examples of polyethyleneimines which may be used in the composition according to the present invention are the EPOMIN products commercially available from Aceto. Suitable examples of EPOMIN polyethyleneimines include EPOMIN SP-006, EPOMIN SP-012, EPOMIN SP-018, and EPOMIN P-1000. Suitable polyamines s also be chosen from polyvinylamines. Examples thereof include LUPAMINES 9095, 9030, 9010, 5095, 1595 from BASF.

The polyamine compounds can also be substituted. An example of such a compound is PEG-15 Cocopolyamine from Cognis.

In some cases, the polyamine is chosen from proteins and protein derivatives. Non-limiting examples of suitable proteins and protein derivatives f include those listed at pages 1701 to 1703 of the C.T.F.A. International Cosmetic Ingredient Dictionary and Handbook, $8^{th}$ edition, vol. 2, (2000), which is incorporated herein by reference in its entirety. In some cases, the at least one polyamine is chosen from wheat protein, soy protein, oat protein, collagen, and keratin protein.

The polyamine may be an alkoxylated polyamine. The alkoxylated polyamines may be chosen from amine compounds having at least two amino groups and at least one degree of alkoxylation. The alkoxylation is provided by an alkylene oxide group which may be chosen from ethylene oxide and propylene oxide. Non-limiting examples of suitable alkoxylated polyamines include compounds corresponding to the following formula:

NH$_2$R(R'CHCH$_2$O)$_x$(R'CHCH$_2$O)$_y$(R'CHCH$_2$O)$_z$—RNH$_2$ wherein R represents a —CH2-, —CH$_2$CH$_2$—, —CHCH$_3$— or —C(CH$_3$)$_2$— group, or a hydrocarbon radical containing at least 3 carbon atoms that is linear or branched, acyclic or cyclic, saturated or unsaturated, aliphatic or aromatic, substituted or unsubstituted; x, y, and z independently of one another, represent numbers of from 0 to about 100; R' represents hydrogen, or an alkyl group, preferably a methyl group; and The sum of x+y+z is at least 1. In some cases, R is a linear or branched, acyclic alkyl or alkenyl group or an alkyl phenyl group; x, y, and z independently of one another, preferably represent numbers ranging from 2 to 100.

Non-limiting examples of the alkoxylated polyamines include, for example, tetradecyloxypropyl-1,3-diaminopropane; a $C_{12-14}$ alkyl oxypropyl-1,3-diaminopropane; a $C_{12-15}$ alkyloxypropyl amine and other similar materials that are commercially available from Tomah under the tradename of TOMAH DA-17. Other examples of alkoxylated polyamines are diamine compounds belonging to the Jeffamine series such as the JEFFAMINE D and JEFFAMINE ED series available from Huntsman Corporation, Salt Lake City, Utah. Examples of these Jeffamine compounds are JEFFAMINE D230, JEFFAMINE D400, JEFFAMINE D2000, JEFFAMINE D4000, JEFFAMINE HK-511, JEFFAMINE ED600, JEFFAMINE ED900, and JEFFAMINE ED2003. JEFFAMINE D series compounds are amine terminated PPGs (polypropylene glycols) and JEFFAMINE ED series compounds are polyether diamine based with a predominantly PEG (polyethylene glycol) backbone.

Other non-limiting examples of suitable alkoxylated polyamines in the diamine form include compounds corresponding to the following formula:

$$NH_2(CH_2)_xOCH_2CH_2O(CH_2)_xNH_2$$

wherein x is 2 or 3.

Examples of alkoxylated polyamines are diamine compounds belonging to the JEFFAMINE series available from Huntsman Corporation, Salt Lake City, Utah, such as JEFFAMINE EDR148, and JEFFAMINE EDR176.

Additional non-limiting examples of alkoxylated polyamines in the triamine form include compounds corresponding to the following formula:

$$NH_2(CHCH_3CH_2O)_xCH_2C(R)CH_2(OCH_2CHCH_3)_zNH_2$$
$$|$$
$$(CH_2)_n(OCH_2CHCH_3)_yNH_2$$

wherein R is hydrogen, —$CH_2$ or —$C_2H_5$, n=0 or 1, and x, y, and z independently of one another, represent numbers of from 0 to 100 and the sum of x+y+z is at least 1.

Examples of alkoxylated polyamines are triamine compounds belonging to the JEFFAMINE series such as the JEFFAMINE T series available from Huntsman Corporation, Salt Lake City, Utah. Examples of the JEFFAMINE T series compounds are JEFFAMINE T403, JEFFAMINE T3000, and JEFFAMINE T5000. JEFFAMINE T series compounds are triamines made by reacting PO with a triol initiator followed by aminating the terminal hydroxyl groups.

Alkylamines and Alkanolamines

The one or more alkylamines and/or one or more alkanolamines that may be included in the compositions include compounds of formula (II):

$$NR_3R_4R_5 \qquad (II)$$

wherein $R_3$, $R_4$ and $R_5$ are independently H, $C_1$-$C_{40}$ alkyl, $C_1$-$C_{40}$ monohydroxyalkyl or $C_2$-$C_{40}$ polyhydroxyalkyl, provided that at least one of $R_3$, $R_4$ and $R_5$ is an alkyl or mono or polyhydroxyalkyl. In some cases, $R_3$, $R_4$ and $R_5$ are independently H, $C_1$-$C_2$ alkyl, $C_1$-$C_{20}$ monohydroxyalkyl or $C_2$-$C_{20}$ polyhydroxyalkyl, provided that at least one of $R_3$, $R_4$ and $R_5$ is an alkyl or mono or polyhydroxyalkyl. Finally, $R_3$, $R_4$ and $R_5$ may independently be H, $C_1$-$C_{10}$ alkyl, $C_1$-$C_{10}$ monohydroxyalkyl or $C_2$-$C_{10}$ polyhydroxyalkyl, provided that at least one of $R_3$, $R_4$ and $R_5$ is an alkyl or mono or polyhydroxyalkyl.

Non-limiting examples of alkanolamines include monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol, tris(hydroxymethylamino)methane, and mixtures thereof. In some cases, the compositions include at least monoethanol amine. In some cases, the compositions include at least monoethanolamine.

Further non-limiting examples of alkylamines include aliphatic amine compounds corresponding to the following formula and their salts:

$$RN(R')_2$$

wherein R is a hydrocarbon radical containing at least 6 carbon atoms. In addition, R can be linear or branched, acyclic or cyclic, saturated or unsaturated, aliphatic or aromatic, substituted or unsubstituted. Typically, R is a linear or branched, acyclic alkyl or alkenyl group or an alkyl phenyl group; and the groups R', which may be identical or different, represent H or a hydrocarbon radical containing less than 6 carbon atoms. In addition, the groups R', which may be identical or different, are linear or branched, acyclic or cyclic, saturated or unsaturated, substituted or unsubstituted. In some cases, the groups R', which may be identical or different, are H or a methyl group.

In some cases, alkylamines include, but are not limited to the following examples: dimethyl lauramine, dimethyl behenamine, dimethyl cocamine, dimethyl myristamine, dimethyl palmitamine, dimethyl stearamine, dimethyl tallowamine, dimethyl soyamine, stearamine, soyamine, cocamine, lauramine, palmitamine, oleamine, tallow amine and mixtures thereof.

Other non-limiting examples of alkyl monoamines include amidoamine compounds corresponding to the following formula and their salts:

$$RCONHR'N(R'')_2$$

wherein: R is a hydrocarbon radical containing at least 6 carbon atoms. In addition, R can be linear or branched, acyclic or cyclic, saturated or unsaturated, aliphatic or aromatic, substituted or unsubstituted. Typically, R is a linear or branched, acyclic alkyl or alkenyl group or an alkyl phenyl group; and R' is a divalent hydrocarbon radical containing less than 6 carbon atoms, or 2 or 3 carbon atoms, and R'' is H or a hydrocarbon radical containing less than 6 carbon atoms. In addition, R'' is linear or branched, acyclic or cyclic, saturated or unsaturated, substituted or unsubstituted. Typically, R'' is a linear or branched, acyclic alkyl or alkenyl group. In some cases, R'' is H or a methyl group.

Examples of amidoamines that are useful in the compositions of the instant disclosure include, but are not limited to the following: oleamidopropyl dimethylamine, stearamidopropyl dimethylamine, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palmitamidopropyl dimethylamine, ricinoleamidopropyl dimethylamine, soyamidopropyl dimethylamine, wheat germamidopropyl dimethylamine, sunflowerseedamidopropyl dimethylamine, almondamidopropyl dimethylamine, avocadoamidopropyl dimethylamine, babassuamidopropyl dimethylamine, cocamidopropyl dimethylamine, minkamidopropyl dimethylamine, oatamidopropyl dimethylamine, sesamidopropyl dimethylamine, tallamidopropyl dimethylamine, brassicaamidopropyl dimethylamine, olivamidopropyl dimethylamine, palmitamidopropyl dimethylamine, stearamidoethyldiethylamine, and mixtures thereof.

Additional Amines

Additional amines that may be useful include alkoxylated monoamines. The alkoxylated monoamines are compounds having an amino group and at least one degree of alkoxylation. The alkoxylation is provided by an alkylene oxide group which is often chosen from ethylene oxide and propylene oxide.

Non-limiting examples of suitable alkoxylated monoamines include compounds corresponding to the following formula:

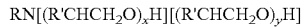
$RN[(R'CHCH_2O)_xH][(R'CHCH_2O)_yH]$ wherein R is a hydrocarbon radical containing at least 6 carbon atoms. R can be linear or branched, acyclic or cyclic, saturated or unsaturated, aliphatic or aromatic, substituted or unsubstituted; x and y, independently of one another, represent numbers of from 0 to 100 provided that the sum of x+y is >0; the groups R', which may be identical or different, represent hydrogen, or an alkyl group such as a methyl group. Typically, R is a linear or branched, acyclic alkyl or alkenyl group or an alkyl phenyl group; x and y, independently of one another, are each typically a number from 0 to 30. Typically, one R' group is hydrogen, and the other one is methyl.

Non-limiting examples of alkoxylated monoamines include PEG-2 Cocamine, PEG-3 Cocamine, PEG-5 Cocamine, PEG-10 Cocamine, PEG-15 Cocamine, PEG-20 Cocamine, PEG-2 Lauramine, PEG-12 Palmitamine, PEG-2 Rapeseedamine, PEG-2 Oleamine, PEG-5 Oleamine, PEG-6 Oleamine, PEG-10 Oleamine, PEG-15 Oleamine, PEG-20 Oleamine, PEG-25 Oleamine, and PEG-30 Oleamine. Other examples are alkoxylated derivatives of soyamine, stearamine and tallow amine.

Other non-limiting examples of suitable alkoxylated monoamines include compounds corresponding the following formula:

$RNR''[(R'CHCH_2O)_xH]$ wherein R is a hydrocarbon radical containing at least 6 carbon atoms. R can be linear or branched, acyclic or cyclic, saturated or unsaturated, aliphatic or aromatic, substituted or unsubstituted; x represents a number of from 1 to 100; R' represents hydrogen, or an alkyl group such as in particular a methyl group; and R'' is a hydrogen or a hydrocarbon radical. Typically, R is a linear or branched, acyclic alkyl or alkenyl group or an alkyl phenyl group; x is typically a number from 1 to 30. When R'' is a hydrocarbon radical group, this group may be linear or branched, saturated or unsaturated, substituted or unsubstituted. The hydrocarbon radical represented by R'' may also contain an alkoxylated moiety (as defined by $[(R'CHCH_2O)_yH]$), and/or heteroatoms such as nitrogen. When R'' contains at least one alkoxylated moiety, the total number of alkoxylation in the formula may range from 1 to 120. Examples of alkoxylated monoamines include PEG-3 Tallow Aminopropylamine, PEG-10 Tallow Aminopropylamine, PEG-15 Tallow Aminopropylamine, and PEG-105 Behenyl Propylenediamine.

Additional non-limiting examples of alkoxylated monoamines include compounds corresponding to the following formula:

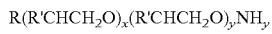
$R(R'CHCH_2O)_x(R'CHCH_2O)_yNH_y$ wherein R is a hydrocarbon radical containing at least 6 carbon atoms. R can be linear or branched, acyclic or cyclic, saturated or unsaturated, aliphatic or aromatic, substituted or unsubstituted; x and y, independently of one another, represent numbers of from 0 to 100 with the proviso that the sum of x+y is >0; the groups R', which may be identical or different, represent hydrogen, or an alkyl group such as in particular a methyl group. Typically, R is a linear or branched, acyclic alkyl or alkenyl group or an alkyl phenyl group; x and y, independently of one another, are each typically a number from 0 to 30. Examples of alkoxylated monoamines include polyetheramines containing a monoamine group. These polyetheramines are commercially available from Hunstman under the tradename JEFFAMINE (M series such as M-600, M-1000, M-2005 and M-2070) and SURFONAMINE series (B-60, B-100, B-200, L-100, L-200, L-207, L-300).

The total amount of the one or more amines may vary, but in some cases, the total amount of the one or more amines is about 0.1 to about 50 wt. %, based on the total weight of the hair treatment composition. In some cases, the total amount of the one or more amines is about 0.1 to about 50 wt. %, about 0.1 to about 30 wt. %, about 0.1 to about 25 wt. %, about 0.1 to about 20 wt. %, about 0.1 to about 15 wt. %, about 0.1 to about 10 wt. %, about 0.5 to about 35 wt. %, about 0.5 to about 30 wt. %, about 0.5 to about 25 wt. %, about 0.5 to about 20 wt. %, about 0.5 to about 15 wt. %, about 0.5 to about 10 wt. %, about 1 to about 35 wt. %, about 1 to about 30 wt. %, about 1 to about 25 wt. %, about 1 to about 20 wt. %, about 1 to about 15 wt. %, about 1 to about 10 wt. %, or about 1 to about 5 wt. %.

Fructan Polysaccharides

Fructan polysaccharides (also referred to as just "fructan") are polymers of fructose molecules. Fructan polysaccharides include inulin polysaccharides (also referred to as just "inulin") and levan polysaccharide (also referred to as just "levan"). In some instances, the leave-on hair styling compositions include inulin polysaccharides; in some cases the leave-on hair styling compositions include levan polysaccharides; but in some cases the leave-on hair styling compositions may include both inulin and levan polysaccharides.

The total amount of the one or more fructan polysaccharides can vary, but is typically about 0.1 to about 40 wt. %, based on the total weight of the leave-on hair styling composition. The total amount of the one or more fructan polysaccharides may be about 0.1 to about 30 wt. %, about 0.1 to about 20 wt. %, about 0.1 to about 15 wt. %, about 0.1 to about 10 wt. %, about 0.1 to about 5 wt. %, about 1 to about 40 wt. %, about 1 to about 30 wt. %, about 1 to about 20 wt. %, about 1 to about 15 wt. %, about 1 to about 10 wt. %, or about 1 to about 5 wt. %.

Inulin refers to a class of polysaccharides produced by a variety of plants, and is an example of a fructan polysaccharide (also referred to as just "fructan") are polymers of fructose molecules. Inulin is commonly extracted from chicory root, and may contain (2→1) linked β-d-fructosyl residues (n=2-60), usually with an (1↔2) α-d-glucose end group. The inulin may be present in amounts ranging from about 0.1, 0.2, 0.3, 0.4, 0.5, 0.6, 0.7, 0.8, 0.9, 1, 1.1, 1.2, 1.3, 1.4, or 1.5 to about 1.5, 2, 2.5, 3, 3.5, 4, 4.5, 5, 6, 7, 8, 9 or 10 wt. % by total weight of the composition. In further embodiments, the inulin is present in an amount of from about 0.1 to about 10 wt. %, or about 0.5 to about 2.5 wt. %.

Prosolvent

As used herein "prosolvent" refers to a solvent system which enhances the performance of the composition by enhancing penetration of the active ingredients into the hair. In one or more embodiments, the prosolvent comprises one or more glycol compounds. In further embodiments, the glycol compounds are selected from the group consisting of hexylene glycol, butylene glycol, propylene glycol, and combinations thereof.

In one or more embodiments, the prosolvent comprises a mixture of two ingredients in a ratio ranging from about 1:2 to about 2:1, or more specifically 1:1. In some embodiments, the prosolvent comprises hexylene glycol and butylene glycol. In one or more embodiments, the prosolvent comprises propylene glycol in addition to hexylene glycol and butylene glycol.

While not wishing to be bound to any particular theory, it is thought that the presence of the prosolvent increases the efficacy of penetrating actives such as maleic acid. The prosolvent may also act as a surfactant and assists in stabilizing the emulsion. Emulsion stability is a particularly important effect when low pH ingredients are present (e.g., maleic acid) because such low pH ingredients can have a negative effect on emulsion stability. Thus, it is thought that the prosolvent works to counteract the negative effect of low pH ingredients on emulsion stability as well as assisting active penetration to the cortex.

Other Components

In one or more embodiments, the hair treatment compositions described in may contain one or more additional ingredients. Examples include, but are not limited to surfactants, cationic conditioning agents, silicones, film formers, other polymers, fragrance and preservatives. Additional details regarding such additional ingredients follows below.

Surfactants

Cationic Surfactants

The term "cationic surfactant" means a surfactant that is positively charged when it is contained in the composition according to the disclosure. This surfactant may bear one or more positive permanent charges or may contain one or more functions that are cationizable in the composition according to the disclosure.

Non-limiting examples of cationic surfactants include behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride(Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

Anionic Surfactants

The term "anionic surfactant" means a surfactant comprising, as ionic or ionizable groups, only anionic groups. These anionic groups are chosen preferably from the groups $CO_2H$, $CO_2^-$, $SO_3H$, $SO_3^-$, $OSO_3H$, $OSO_3^-O_2PO_2H$, $O_2PO_2H$ and $O_2PO_2^{2-}$.

The anionic surfactant(s) that may be used may be alkyl sulfates, alkyl ether sulfates, alkylamido ether sulfates, alkylaryl polyether sulfates, monoglyceride sulfates, alkylsulfonates, alkylamide sulfonates, alkylarylsulfonates, alpha-olefin sulfonates, paraffin sulfonates, alkylsulfosuccinates, alkyl ether sulfosuccinates, alkylamide sulfosuccinates, alkyl sulfoacetates, acylsarcosinates, acylglutamates, alkylsulfosuccinamates, acylisethionates and N-acyltaurates, salts of alkyl monoesters and polyglycoside-polycarboxylic acids, acyllactylates, salts of D-galactoside uronic acids, salts of alkyl ether carboxylic acids, salts of alkyl aryl ether carboxylic acids, and salts of alkylamido ether carboxylic acids; or the non-salified forms of all of these compounds, the alkyl and acyl groups of all of these compounds containing from 6 to 24 carbon atoms and the aryl group denoting a phenyl group. Some of these compounds may be oxyethylenated and then preferably comprise from 1 to 50 ethylene oxide units.

The salts of $C_6$-$C_{24}$ alkyl monoesters of polyglycoside-polycarboxylic acids may be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfo succinates.

When the anionic surfactant(s) are in salt form, they may be chosen especially from alkali metal salts such as the sodium or potassium salt and preferably the sodium salt, ammonium salts, amine salts and in particular amino alcohol salts, or alkaline-earth metal salts such as the magnesium salt.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts. Alkali metal or alkaline-earth metal salts and in particular the sodium or magnesium salts may be used.

Mention is also made of ($C_6$-$C_{24}$)alkyl sulfates, ($C_6$-$C_{24}$) alkyl ether sulfates, which are optionally ethoxylated, comprising from 2 to 50 ethylene oxide units, and mixtures thereof, in particular in the form of alkali metal salts or alkaline-earth metal salts, ammonium salts or amino alcohol salts. In some cases, the anionic surfactant(s) are chosen from ($C_{10}$-$C_{20}$)alkyl ether sulfates, and in particular sodium lauryl ether sulfate containing 2.2 mol of ethylene oxide.

Amphoteric Surfactants

Amphoteric surfactants useful in the cosmetic compositions disclosed herein may be chosen from betaines, sultaines, amphoacetates, amphoproprionates, and mixtures thereof. More typically, betaines and amphoproprionates are used, and most typically betaines. Betaines which can be used in the current compositions include those having the formulas below:

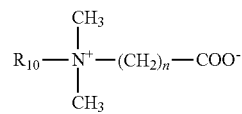

-continued $$R_{10}-\underset{\underset{O}{\|}}{C}-\underset{\underset{H}{|}}{N}-CH_2-CH_2-\underset{\underset{H}{|}}{\overset{\overset{CH_2-CH_2-OH}{|}}{N^+}}-CH_2COO^-$$

$$R_{10}-\underset{\underset{CH_3}{|}}{\overset{\overset{CH_3}{|}}{N^+}}-(CH_2)_n-SO_3^-$$

$$R_{10}-\underset{\underset{O}{\|}}{C}-\underset{\underset{H}{|}}{N}-(CH_2)_n-\underset{\underset{CH}{|}}{\overset{\overset{CH_3}{|}}{N^+}}-CH_2COO^-$$

wherein
$R^{10}$ is an alkyl group having 8-18 carbon atoms; and
n is an integer from 1 to 3.

Particularly useful betaines include, for example, coco betaine, cocoamidopropyl betaine, lauryl betaine, laurylhydroxy sulfobetaine, lauryldimethyl betaine, cocoamidopropyl hydroxysultaine, behenyl betaine, capryl/capramidopropyl betaine, lauryl hydroxysultaine, stearyl betaine, and mixtures thereof. Typically, the at least one betaine compound is selected from the group consisting of coco betaine, cocoamidopropyl betaine, behenyl betaine, capryl/capramidopropyl betaine, lauryl betaine, and mixtures thereof, and more typically coco betaine.

Hydroxyl sultaines useful in the compositions of the invention include the following $$R\underset{\underset{O}{\|}}{C}-NH(CH_2)_3-\underset{\underset{CH_3}{|}}{\overset{\overset{CH_3}{|}}{N^+}}-CH_2\underset{\underset{OH}{|}}{CH}CH_2SO_3^-$$

wherein
R is an alkyl group having 8-18 carbon atoms.

Useful alkylamphoacetates include those having the formula $$R-\underset{\underset{NH}{}}{\overset{\overset{O}{\|}}{C}}-CH_2CH_2-\underset{}{N}(CH_2CH_2OH)-CH_2-\overset{\overset{O}{\|}}{C}-O^-Na^+$$

wherein
R is an alkyl group having 8-18 carbon atoms.
useful alkyl amphodiacetates include those having the formula $$R-\underset{\underset{CH_2CH_2OH}{|}}{N(COCH_2O^-Na^+)}-CH_2CH_2-N(CH_2COO^-Na^+)$$

wherein
R is an alkyl group having 8-18 carbon atoms.

The amphoteric surfactants of the present disclosure may be optionally quaternized secondary or tertiary aliphatic amine derivatives, in which the aliphatic group is a linear or branched chain comprising from 8 to 22 carbon atoms, said amine derivatives containing at least one anionic group, for instance a carboxylate, sulfonate, sulfate, phosphate or phosphonate group.

Non-Ionic Surfactants

Nonionic surfactants are compounds well known in themselves (see, e.g., in this regard, "Handbook of Surfactants" by M. R. Porter, Blackie & Son publishers (Glasgow and London), 1991, pp. 116-178), which is incorporated herein by reference in its entirety.

The nonionic surfactant can be, for example, selected from alcohols, alpha-diols, alkylphenols and esters of fatty acids, these compounds being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and mixtures thereof.

The nonionic surfactants may preferably be chosen from polyoxyalkylenated or polyglycerolated nonionic surfactants. The oxyalkylene units are more particularly oxyethylene or oxypropylene units, or a combination thereof, and are preferably oxyethylene units.

In some cases, the nonionic surfactant may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and mixtures thereof.

Examples of ethoxylated fatty esters that may be mentioned include the adducts of ethylene oxide with esters of lauric acid, palmitic acid, stearic acid or behenic acid, and mixtures thereof, especially those containing from 9 to 100 oxyethylene groups, such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); polyethylene glycol 100 EO monostearate (CTFA name: PEG-100 stearate); and mixtures thereof.

As glyceryl esters of fatty acids, glyceryl stearate (glyceryl mono-, di- and/or tristearate) (CTFA name: glyceryl stearate) or glyceryl ricinoleate and mixtures thereof can in particular be cited.

As glyceryl esters of $C_8$-$C_{24}$ alkoxylated fatty acids, polyethoxylated glyceryl stearate (glyceryl mono-, di- and/or tristearate) such as PEG-20 glyceryl stearate can for example be cited.

Mixtures of these surfactants, such as for example the product containing glyceryl stearate and PEG-100 stearate, marketed under the name ARLACEL 165 by Uniqema, and the product containing glyceryl stearate (glyceryl mono- and distearate) and potassium stearate marketed under the name TEG1 N by Goldschmidt (CTFA name: glyceryl stearate SE), can also be used.

Cationic Conditioning Agents

The cationic conditioning agents that may be employed in the compositions of the present disclosure can be a mono-alkyl quaternary amine, such as stearyltrimonium chloride, soyatrimonium chloride or coco-ethyldimonium ethosulfate. Other suitable cationic conditioning agents include, but are not limited to, behentrimonium chloride, dialkyl quaternary amines, such as dicetyldimonium chloride, dicocodimethyl ammonium chloride or distearyldimethyl ammonium chloride; and polyquaternium compounds, such as Polyquaternium-6, Polyquaternium-22 or Polyquaternium-5.

For example, cationic conditioning agents may be chosen from polyquaterium-10 (also called quaternized polyhydroxyethyl cellulose), cetrimonium chloride (also called cetyl trimethyl ammonium chloride, CTAC), behentrimonium chloride (also known as docosyl trimethyl ammonium chloride), behentrimonium methosulfate, steartrimonium chloride, stearalkonium chloride, dicetyldimonium chloride, hydroxypropyltrimonium chloride, cocotrimonium methosulfate, olealkonium chloride, steartrimonium chloride, babassuamidopropalkonium chloride, brassicamidopropyl dimethylamine, Quaternium-91, Salcare/PQ-37, Quaternium-22, Quaternium-87, Polyquaternium-4, Polyquaternium-6, Polyquaternium-11, Polyquaternium-44, Polyquaternium-67, amodimethicone, lauryl betaine, Polyacrylate-1 Crosspolymer, steardimonium hydroxypropyl hydrolyzed wheat protein, behenamidopropyl PG-dimonium chloride, lauryldimonium hydroxypropyl hydrolyzed soy protein, aminopropyl dimethicone, Quaterium-8, and dilinoleamidopropyl dimethylamine dimethicone PEG-7 phosphate.

In some instances, the cationic conditioning agents are cationic polymers. The term "cationic polymer" means any polymer comprising at least one cationic group and/or at least one group that may be ionized into a cationic group.

Particularly useful cationic polymers in the present invention include, but are not limited to, polyquaternium 4, polyquaternium 6, polyquaternium 7, polyquaternium 10, polyquaternium 11, polyquaternium 16, polyquaternium 22, polyquaternium 28, polyquaternium 32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, and guar hydroxypropyltrimonium chloride.

Particularly preferred cationic polymers of the present invention include POLYMER JR-125, POLYMER JR-400, Polymer JR-30M hydroxyethyl cellulosic polymers (polyquaternium 10) available from AMERCHOL; JAGUAR C® 13-S, guar hydroxypropyltrimonium chloride, available from Rhodia; and MERQUAT® 100 and 280, a dimethyl dialkyl ammonium chloride (polyquaternium 6) available from Nalco.

The cationic polymer is generally present in an amount of from greater than 0% to about 15%, preferably from about 0.5% to about 10% by weight, and more preferably from about 1% to about 5% by weight, based on the total weight of the composition.

Cationic polymers useful herein include polyquaternium 4, polyquaternium 6, polyquaternium 7, polyquaternium 10, polyquaternium 11, polyquaternium 16, polyquaternium 22, and polyquaternium 32. Cationic polymers useful in the present invention include, but are not limited to, polyquaternium 4, polyquaternium 6, polyquaternium 7, polyquaternium 10, polyquaternium 11, polyquaternium 16, polyquaternium 22, polyquaternium 28, polyquaternium 32, and guar hydroxypropyltrimonium chloride. Preferred cationic polymers include POLYMER JR-125, POLYMER JR-400, Polymer JR-30M hydroxyethyl cellulosic polymers (polyquaternium 10) available from AMERCHOL; JAGUAR C13-S, guar hydroxypropyltrimonium chloride, available from Rhodia; and MERQUAT 100 and 280, a dimethyl dialkyl ammonium chloride (polyquaternium 6) available from Nalco.

Oils

The hair styling composition may include one or more oils, for example, silicone oils, fluoro oils, hydrocarbon-based oils, etc. The term "oil" means any fatty substance which is in liquid form at room temperature (20-25° C.) and at atmospheric pressure (760 mmHg). Often, at least one of the oils in the cosmetic composition is part of an oily phase. An "oily phase" is a phase comprising at least one oil that may include additional liposoluble and lipophilic ingredients and the fatty substances. The oily phase can be combined with an aqueous phase in an emulsion. Oil that is suitable for use herein may be volatile or non-volatile. The term "volatile oil" relates to oil that is capable of evaporating on contact with the skin or a keratin fiber in less than one hour, at room temperature and atmospheric pressure. The volatile oil(s) are liquid at room temperature and have a non-zero vapor pressure, at room temperature and atmospheric pressure, ranging in particular from 0.13 Pa to 40 000 Pa ($10^{-3}$ to 300 mmHg). The term "non-volatile oil" relates to oil which remains on the skin or the keratin fiber, at room temperature and atmospheric pressure, for at least several hours and which in particular has a vapor pressure of less than $10^{-3}$ mmHg (0.13 Pa).

The term "silicone oil" relates to oil comprising at least one silicon atom, and especially at least one Si—O group. The term "fluoro oil" relates to oil comprising at least one fluorine atom. The term "hydrocarbon-based oil" relates to oil comprising mainly hydrogen and carbon atoms. Hydrocarbon-based oil may be animal hydrocarbon-based oil, plant hydrocarbon-based oil, mineral hydrocarbon-based oil or a synthetic hydrocarbon-based oil. Further, suitable oil may be a mineral hydrocarbon-based oil, a plant hydrocarbon-based oil, or a synthetic hydrocarbon-based oil.

Silicone Oils

The cosmetic compositions described herein may comprise one or more silicone oils. Non-limiting examples of silicone oils include dimethicone, cyclomethicone, polysilicone-11, phenyl trimethicone, trimethylsilylamodimethicone, and stearoxytrimethylsilane. In some cases, the cosmetic composition includes dimethicone, and optionally additional oils, including additional silicone oils. Typically, the one or more silicone oils is a non-volatile silicon oil. In some embodiments, the silicone oil is polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl(trimethylsiloxy)diphenylsiloxanes, diphenyl dimethicones, diphenyl(methyldiphenyl)trisiloxanes or (2-phenylethyl)trimethylsiloxysilicates.

Other examples of silicone oils that may be mentioned include volatile linear or cyclic silicone oils, especially those with a viscosity 8 centistokes ($8 \times 10^6$ m$^2$/s) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Fluoro Oils

The cosmetic compositions described herein may comprise one or more fluoro oils. For example, the onee or more fluoro oil may be selected from the group consisting of perfluoromethylcyclopentane, perfluoro-1,3-dimethylcyclohexane, dodecafluoropentane, tetradecafluorohexane, bromoperfluorooctyl, nonafluoromethoxybutane, nonafluoroethoxyisobutane and 4-trifluoromethylperfluoromorpholine. Volatile fluoro oils, such as nonafluoromethoxybutane, decafluoropentane, tetradecafluorohexane, dodecafluoropentane, may also be used.

Hydrocarbon-Based Oils

The cosmetic compositions described herein may comprise one or more hydrocarbon-based oils. For example, the hydrocarbon-based oil may be a saturated hydrocarbon, an unsaturated hydrocarbon, lipids, triglycerides, a natural oil, and/or a synthetic oil. In some embodiments, the compositions include a synthetic oil selected from the group consisting of hydrogenated polyisobutene and hydrogenated polydecene.

The hydrocarbon-based oil may be a non-volatile hydrocarbon-based, such as:

(i) hydrocarbon-based oils of plant origin, such as glyceride triesters, which are generally triesters of fatty acids and of glycerol, the fatty acids of which can have varied chain lengths from $C_4$ to $C_{24}$, it being possible for these chains to be saturated or unsaturated and linear or branched; these oils are in particular wheat germ oil, sunflower oil, grape seed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin seed oil, marrow oil, blackcurrant oil, evening primrose oil, millet oil, barley oil, quinoa oil, rye oil, safflower oil, candlenut oil, passionflower oil, and musk rose oil.

(ii) synthetic ethers containing from 10 to 40 carbon atoms;

(iii) linear or branched hydrocarbons of mineral or synthetic origin, such as petroleum jelly, polydecenes, hydrogenated polyisobutene such as Parleam, and 40 squalane;

(iv) synthetic esters, for instance oils of formula RCOOR' in which R represents a linear or branched fatty acid residue containing from 1 to 40 carbon atoms and R' represents a hydrocarbon-based chain that is especially branched, containing from 1 to 40 carbon atoms on condition that R+R' is ≥10, for instance Purcellin oil (cetearyl octanoate), isopropyl myristate, isopropyl palmitate, $C_{12}$-$C_{15}$ alkyl benzoate, such as the product sold under the trade name Finsolv TN® or Witconol TN® by Witco or Tegosoft TN® by Evonik Goldschmidt, 2-ethylphenyl benzoate, such as the commercial product sold under the name X-Tend 226 by ISP, isopropyl lanolate, hexyl laurate, diisopropyl adipate, isononyl isononanoate, oleyl erucate, 2-ethylhexyl palmitate, isostearyl isostearate, diisopropyl sebacate, such as the product sold under the name of "Dub Dis" by Stearinerie Dubois, octanoates, decanoates or ricinoleates of alcohols or polyalcohols, such as propylene glycol dioctanoate; hydroxylated esters, such as isostearyl lactate or diisostearyl malate; and pentaerythritol esters; citrates or tartrates, such as di(linear $C_{12}$-$C_{13}$ alkyl) tartrates, such as those sold under the name Cosmacol ETI® by Enichem Augusta Industriale, and also di(linear $C_{14}$-$C_{15}$ alkyl) tartrates, such as those sold under the name Cosmacol ETL® by the same company; or acetates;

(v) fatty alcohols that are liquid at room temperature, containing a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol;

(vi) higher fatty acids, such as oleic acid, linoleic acid or linolenic acid;

(vii) carbonates, such as dicaprylyl carbonate, such as the product sold under the name Cetiol CC® by Cognis;

(viii) fatty amides, such as isopropyl N-lauroyl sarcosinate, such as the product sold under the trade name Eldew SL 205® from Ajinomoto; and (ix) essential oils selected from the group consisting of sunflower oil, sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, and ylang ylang.

In certain instances, the non-volatile hydrocarbon-based oils are glyceride triesters and in particular to caprylic/capric acid triglycerides, synthetic esters and in particular isononyl isononanoate, oleyl erucate, $C_{12}$-$C_{15}$ alkyl benzoate, 2-ethylphenyl benzoate and fatty alcohols, such as octyldodecanol.

As volatile hydrocarbon-based oils, mention is made of hydrocarbon-based oils containing from 8 to 16 carbon atoms and in particular of branched $C_8$-$C_{16}$ alkanes, such as $C_8$-$C_{16}$ isoalkanes of petroleum origin (also known as isoparaffins), such as isododecane (also known as 2,2,4,4,6-pentamethylheptane), isodecane or isohexadecane, the oils sold under the Isopar or Permethyl trade names, branched C $C_8$-$C_{16}$ esters, and isohexyl neopentanoate.

Preservatives

One or more preservatives may be included in the compositions described herein for treating hair. Suitable preservatives include, but are not limited to, glycerin containing compounds (e.g., glycerin or ethylhexylglycerin or phenoxyethanol), benzyl alcohol, parabens (methylparaben, ethylparaben, propylparaben, butylparaben, isobutylparaben, etc.), sodium benzoate, ethylenediamine-tetraacetic acid (EDTA), potassium sorbate, and/or grapefruit seed extract, or combinations thereof. More than one preservative may be included in the composition. Other preservatives are known in the cosmetics industries and include salicylic acid, DMDM Hydantoin, Formaldehyde, Chlorphenism, Triclosan, Imidazolidinyl Urea, Diazolidinyl Urea, Sorbic Acid, Methylisothiazolinone, Sodium Dehydroacetate, Dehydroacetic Acid, Quaternium-15, Stearalkonium Chloride, Zinc Pyrithione, Sodium Metabisulfite, 2-Bromo-2-Nitropropane, Chlorhexidine Digluconate, Polyaminopropyl biguanide, Benzalkonium Chloride, Sodium Sulfite, Sodium Salicylate, Citric Acid, Neem Oil, Essential Oils (various), Lactic Acid, and Vitamin E (tocopherol).

The total amount of the one or more preservatives, when present, may vary. In some cases, the total amount of the one or more preservatives is about 0.01 to about 5 wt. %, about 0.01 to about 4 wt. %, about 0.15 to about 1 wt. %, or about 1 to about 3 wt. %, based on the total weight of the composition.

Suitable components, such as those listed in the instant disclosure (including those listed above), may be included or excluded from the hair styling compositions depending on the specific combination of other components, the form of the compositions, and/or the use of the formulation (e.g., hair spray, cream, paste, conditioner, etc.).

Methods

Another aspect of the invention pertains to methods of using the hair treatment compositions described herein. The methods generally comprise applying any of the hair treatment compositions described to hair. The hair treatment compositions may be useful in a variety of settings, and either for treated or untreated hair. Use on treated hair can include chemically relaxed hair. The hair treatment composition may be applied post relaxer but before neutralizing shampoo, after neutralizing shampoo, in or as a conditioner, or as a leave in treatment after the relaxation process. Use on untreated hair may include as part of a shampoo, part of a conditioner, as a pre-treatment, or after washing the hair as a leave-in treatment.

Methods of treating hair according to the disclosure may include applying a hair treatment composition of the instant disclosure to the hair (wet, damp, or dry hair), allowing the hair treatment to remain on the hair for a sufficient amount of time, and rinsing the hair treatment composition from the hair. The hair treatment composition may be applied to the hair before, during, or after other hair treatment compositions (e.g., a chemical relaxer composition, a shampoo, a conditioner, a lotion, a gel, etc.).

As mentioned previously, the hair treatment compositions are particularly useful for treating chemically treated hair. In some cases, a hair treatment composition is applied to the hair shortly after a chemical treatment composition is rinsed from the hair (e.g., within about 5, 10, 15, 20, or 30 minutes from when the chemical treatment composition is rinsed from the hair), while the hair is still wet or damp. The hair treatment composition may be allowed to remain on the hair for a period of time, for example from about a few seconds (1, 3, 5, or 10 seconds) to about 10, 20, or 30 minutes, or longer. In some cases, the hair treatment composition is applied to the chemically treated hair shortly after a chemical treatment composition is rinsed from the hair; and after applying the hair treatment composition, the hair is subsequently treated with a shampoo and/or a conditioner, or a conditioning shampoo (all-in-one shampoo/conditioner). The hair treatment composition may be rinsed from the hair prior to application of a shampoo and/or a conditioner, or a conditioning shampoo, or it may be allowed to remain on the hair during shampooing and/or conditioning and rinsed from the hair with the shampoo or the conditioner, or with the conditioning shampoo. For example, the hair treatment composition may be applied to the hair and without rinsing the hair treatment from the hair, a shampoo (or conditioner or conditioning shampoo) is subsequently applied to the hair (layered onto the hair treatment composition already applied to the hair). Both compositions (the hair treatment composition and the shampoo, conditioner, or conditioning shampoo) are rinsed from the hair together.

Moreover, the hair treatment composition may be combined with a shampoo and/or a conditioner, or with a conditioning shampoo, prior to application to the hair. Combining the hair treatment compositions with one or more additional hair treatment compositions (e.g., a shampoo, a conditioner, a conditioning shampoo, a rinse, etc.). For instance, the hair treatment composition may be mixed with a shampoo (or conditioner or conditioning shampoo) prior to application to the hair. In this case, the mixture of the shampoo (or conditioner or conditioning shampoo) and the hair treatment composition are simultaneously applied to the hair during the cleansing and/or conditioning process and simultaneously rinsed from the hair. Alternatively, the hair treatment composition may be layered on top of (or lathered into) hair to which a shampoo (or conditioner or conditioning shampoo) has already been applied or vice versa. In this case, the hair treatment composition may be applied to the hair first and without rinsing it from the hair, a shampoo (or conditioner or conditioning shampoo) is then subsequently applied to the hair. Alternatively, the shampoo (or conditioner or conditioning shampoo) may be first applied to the hair and without rinsing the shampoo (or conditioner or conditioning shampoo) from the hair, the hair treatment composition is also applied to the hair. Then, the compositions are simultaneously rinsed from the hair.

Described above is the individual application of a hair treatment composition or the combined or layered application of a hair treatment composition with another composition (e.g., a shampoo, conditioner, conditioning shampoo, etc.). In some cases, a hair treatment composition is individually applied to the hair and also combined or layered with another composition (e.g., a shampoo, conditioner, conditioning shampoo, etc.) that is also applied to the hair. For example, a hair treatment composition may be applied to the hair. Subsequently, with or without rinsing the hair treatment composition from the hair, another composition (e.g., a shampoo, conditioner, conditioning shampoo, etc.) in which the hair treatment composition has been mixed may be applied to the hair.

When combined with another composition (e.g., a shampoo, conditioner, conditioning shampoo, etc.), the hair treatment composition may be mixed with or used with in a ratio of about 1:10 to about 10:1, about 1:5 to about 5:1, about 1:3 to about 3:1, about 1:2 to about 2:1, about 1:1 to about 4:1, about 1:1 to about 3:1, or about 1:1 to about 2:1 (hair treatment composition of the instant disclosure:another composition).

The hair treatment compositions may be allowed to remain on the hair for a minimum amount of time before being rinsed from the hair, but allowing the hair treatment composition to remain on the hair for an extended period of time is not needed. Conveniently, the hair treatment compositions can be applied and allowed to remain on the hair for a period of time that is typical for regular shampooing and/or conditioning. For example, the hair treatment composition (whether combined with another hair treatment composition such as a shampoo or conditioner) may be applied to the hair and allowed to remain on the hair for a few seconds (1, 2, 3, 5, or 10 seconds) up to about 1, 2, 5, 10, 20, or 30 minutes, or longer.

When the hair treatment composition is not applied to the hair, simultaneously with another composition (e.g., a shampoo, conditioner, conditioning shampoo, etc.), the hair treatment composition may be applied to the hair immediately after or before the hair is treated with another composition (e.g., a shampoo, conditioner, conditioning shampoo, etc.). For example, the hair treatment compositions may be applied to the hair within about 1, 2, 5, 10, or 20 minutes before or after another composition is applied to the hair.

Kits

The hair treatment compositions of the instant disclosure may be incorporated into a kit. For example, the kits may include at least one hair treatment composition according to the instant disclosure and one or more additional hair treatment compositions, for example, a hair relaxer composition, a shampoo, a conditioner, etc. The various hair treatment compositions are separately contained in the kits. In some instances, the kits include one or more hair treatment compositions (according the instant disclosure), a shampoo, and/or a conditioner, all of which are separately contained. The kits may also include one or more hair treatment compositions (according the instant disclosure), a chemical relaxer composition, and optionally a shampoo and/or a conditioner. Instructions, mixing components, brushes, gloves, measuring tools, etc., may also be included in the kits.

Implementation of the present disclosure is provided by way of the following examples. The examples serve to illustrate the technology without being limiting in nature.

Example 1

Hair Treatment Composition

| INCI Name | Concentration (wt. %) |
| --- | --- |
| Maleic Acid | 3.00 |
| Lactic Acid | 1.31 |
| Ethanolamine | 1.40 |
| Inulin | 2.91 |
| Hexylene Glycol | 1.50 |
| Butylene Glycol | 1.50 |
| Water | 61.32 |
| Magnesium Sulfate | 1.25 |
| Propylene Glycol | 0.03 |
| Hydrogenated Starch Hydrolysate | 1.05 |
| Silicones | 9.87 |
| Polymers | 3.53 |
| Solvents | 10.09 |
| Misc. (Fragrance, preservative, etc.) | 1.25 |

Example 2

Synergy of Ingredients

Testing was carried out to determine the influence of several ingredients. Several formulas containing a combination of ingredients as shown in the table below were applied to medium bleached hair swatches. The swatches were evaluated by several chemists with a 1-5 rating system for each of the attributes shown in the table. The same amount of each ingredient was used in the comparisons.

| Actives Present | Inulin | Maleic acid | Maleic acid & Prosolvent | Maleic acid & Prosolvent & Inulin |
| --- | --- | --- | --- | --- |
| Strength: Hair mass | | + | + | +++ |
| Strength: Hair body | | + | ++ | +++ |
| Strength: Hair suppleness | | + | ++ | +++ |
| Style: Fiber alignment | ++ | | | +++ |
| Style: Fiber definition | ++ | | | +++ |
| Style: closed ends | + | | | ++ |
| Style: discipline | ++ | | | +++ |
| Style: shine | + | | | ++ |

+ Signal is noticeable
++ Signal is pronounced
+++ Signal is very significant

The results show a synergistic effect when all three of inulin, maleic acid and prosolvent are present in all of the hair attributes.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" (or "comprise," "have," and "include") are used in their open, non-limiting sense.

The terms "a," "an," and "the" are understood to encompass the plural as well as the singular.

Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The salts, for example, the salts of the non-polymeric mono, di, and/or tricarboxylic acids, which are referred to throughout the disclosure may include salts having a counter-ion such as an alkali metal, alkaline earth metal, or ammonium counterion. This list of counterions, however, is non-limiting.

The expression "one or more" means "at least one" and thus includes individual components as well as mixtures/combinations.

Other than in the operating examples, or where otherwise indicated, all numbers expressing quantities of ingredients and/or reaction conditions are to be understood as being modified in all instances by the term "about," meaning within +/−5% of the indicated number.

Some of the various categories of components identified for the various composition described herein, including the hair treatment compositions, may overlap. In such cases where overlap may exist between two or more components, a single overlapping compound does not represent more than one component. For example, a homopolymer of methyl quaternized dimethylaminoethyl methacrylate may be characterized as both a cationic polymer component and a thickening agent component. If a particular composition is described as including both a cationic polymer and a thickening agent, a single homopolymer of methyl quaternized dimethylaminoethyl methacrylate would serve as only the cationic polymer or only the thickening agent (the compound does not serve as both the cationic polymer and the thickening agent in the same composition).

All percentages, parts and ratios herein are based upon the total weight of the compositions of the present invention, unless otherwise indicated.

"Keratinous substrates" as used herein, includes, but is not limited to keratin fibers such as hair and/or scalp on the human head.

"Conditioning" as used herein means imparting to one or more hair fibers at least one property chosen from combability, moisture-retentivity, luster, shine, and softness. The state of conditioning can be evaluated by any means known in the art, such as, for example, measuring, and comparing, the ease of combability of the treated hair and of the untreated hair in terms of combing work (gm-in), and consumer perception.

The term "treat" (and its grammatical variations) as used herein refers to the application of the compositions of the present disclosure onto the surface of keratinous substrates such as hair. The term "treat," and its grammatical variations, relates to contacting hair with the hair treatment compositions of the present disclosure.

The term "stable" as used herein means that the composition does not exhibit phase separation and/or crystallization for a period of time, for example, for at least 1 day (24 hours), one week, one month, or one year.

"Volatile", as used herein, means having a flash point of less than about 100° C.

"Non-volatile", as used herein, means having a flash point of greater than about 100° C.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically 1, 2, 3, 4 and 5, as well as sub ranges such as 2-5, 3-5, 2-3, 2-4, 1-4, etc.

The term "substantially free" or "essentially free" as used herein means that there is less than about 5% by weight of a specific material added to a composition, based on the total weight of the compositions. Nonetheless, the compositions may include less than about 3 wt. %, less than about 2 wt. %, less than about 1 wt. %, less than about 0.5 wt. %, less than about 0.1 wt. %, or none of the specified material.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A hair treatment composition comprising:
   at least 0.5 wt. % of one or more carboxylic acids chosen from non-polymeric mono, di, or tricarboxylic acids, salts thereof, or mixtures thereof;
   one or more amines chosen from diamines, polyamines, alkylamines, alkanolamines, or mixtures thereof;
   one or more fructan polysaccharides chosen from levan polysaccharides;
   one or more prosolvents; and
   water.

2. The hair treatment composition of claim 1, wherein the one or more carboxylic acids comprises a dicarboxylic acid and/or a salt thereof.

3. The hair treatment composition of claim 2, wherein the dicarboxylic acid is chosen from oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, salts thereof, or mixtures thereof.

4. The hair treatment composition of claim 3, wherein the at least one dicarboxylic acid is maleic acid, malonic acid, salts thereof, or mixtures thereof.

5. The hair treatment composition of claim 1, comprising at least one tricarboxylic acid chosen from citric acid, isocitric acid, aconitric acid, propane-1,2,3-tricarboxylic acid, benzene-1,3,5-tricarboxylic acid, salts thereof, or mixtures thereof.

6. The hair treatment composition of claim 5, wherein the at least one tricarboxylic acid is citric acid, a salt thereof, or a mixture thereof.

7. The hair treatment composition of claim 1, wherein the total amount of the one or more carboxylic acids chosen from non-polymeric mono, di, or tricarboxylic acids, salts thereof, or mixtures thereof ranges from 0.5 wt. % to about 20 wt. %, based on the total weight of the hair treatment composition.

8. The hair treatment composition of claim 1, comprising one or more alkylamine and/or alkanolamine compound of formula (II):

$$NR_3R_4R_5 \quad (II)$$

wherein $R_3$, $R_4$, and $R_5$ are independently H, $C_1$-$C_{40}$ alkyl, $C_1$-$C_{40}$ monohydroxyalkyl, or $C_2$-$C_{40}$ polyhydroxyalkyl, provided that at least one of $R_3$, $R_4$, and $R_5$ is an alkyl or monohydroxyalkyl or polyhydroxyalkyl.

9. The hair treatment composition of claim 8, comprising one or more alkanolamines chosen from monoethanolamine, diethanolamine, triethanolamine, monoisopropanolamine, diisopropanolamine, N-dimethylamino-ethanolamine, 2-amino-2-methyl-1-propanol, triisopropanolamine, 2-amino-2-methyl-1,3-propanediol, 3-amino-1,2-propanediol, 3-dimethylamino-1,2-propanediol, tris(hydroxymethylamino)methane, or mixtures thereof.

10. The hair treatment composition of claim 9, comprising monoethanolamine.

11. The hair treatment composition of claim 1, wherein the total amount of the one or more amines ranges from about 1 wt. % to about 20 wt. %, based on the total weight of the hair treatment composition.

12. The hair treatment composition of claim 1, further comprising one or more inulin polysaccharides.

13. The hair treatment composition of claim 1, wherein the total amount of the one or more fructan polysaccharides ranges from about 1 wt. % to about 5 wt. %, based on the total weight of the hair treatment composition.

14. The hair treatment composition of claim 1, wherein the one or more prosolvents is chosen from hexylene glycol, butylene glycol, propylene glycol, or mixtures thereof.

15. A hair treatment composition comprising:
about 2 wt. % to about 4 wt. % of maleic acid, a salt thereof, or a mixture thereof;
about 1 wt. % to about 3 wt. % of monoethanolamine;
about 1 wt. % to about 5 wt. % of one or more levan polysaccharides;
about 2 wt. % to about 4 wt. % of a mixture of hexylene glycol and butylene glycol; and
water.

16. A method of treating hair, the method comprising:
applying to the hair a hair treatment composition comprising:
at least 0.5 wt. % of one or more carboxylic acids chosen from non-polymeric mono, di, or tricarboxylic acids, salts thereof, or mixtures thereof;
one or more amines chosen from diamines, polyamines, alkylamines, alkanolamines, or mixtures thereof;
one or more fructan polysaccharides chosen from levan polysaccharides;
one or more prosolvents; and
water.

17. The method of claim 16, wherein the composition is applied to hair as part of a shampoo or conditioning routine.

18. The method of claim 17, wherein the composition is applied after a chemical relaxer is applied to the hair.

19. A method of treating hair, the method comprising:
applying to the hair a hair treatment composition comprising:
about 2 wt. % to about 4 wt. % of maleic acid, a salt thereof, or a mixture thereof;
about 1 wt. % to about 3 wt. % of monoethanolamine;
about 1 wt. % to about 5 wt. % of one or more levan polysaccharides;
about 2 wt. % to about 4 wt. % of a mixture of hexylene glycol and butylene glycol; and
water.

* * * * *